United States Patent [19]

Kandimalla et al.

[11] Patent Number: 5,693,773
[45] Date of Patent: Dec. 2, 1997

[54] TRIPLEX-FORMING ANTISENSE OLIGONUCLEOTIDES HAVING ABASIC LINKERS TARGETING NUCLEIC ACIDS COMPRISING MIXED SEQUENCES OF PURINES AND PYRIMIDINES

[75] Inventors: Ekambar Kandimalla, Worcester; Sudhir Agrawal, Shrewsbury, both of Mass.

[73] Assignee: Hybridon Incorporated, Cambridge, Mass.

[21] Appl. No.: 473,096

[22] Filed: Jun. 7, 1995

[51] Int. Cl.$^6$ .................... C07H 19/00; C07H 21/04; C12Q 1/68; A61K 48/00
[52] U.S. Cl. .................... 536/22.1; 536/24.5; 435/6; 435/5; 435/91.1; 514/44
[58] Field of Search .................... 514/44; 536/24.5, 536/22.1; 435/6, 5, 91.1

[56] References Cited

U.S. PATENT DOCUMENTS

| | | | |
|---|---|---|---|
| 4,689,320 | 8/1987 | Kaji | 514/44 |
| 4,806,463 | 2/1989 | Goodchild et al. | 435/5 |
| 5,015,570 | 5/1991 | Scangos et al. | 435/6 |
| 5,107,065 | 4/1992 | Shewmaker et al. | 800/205 |
| 5,194,428 | 3/1993 | Agrawal et al. | 514/44 |
| 5,399,676 | 3/1995 | Froehler | 536/23.1 |
| 5,473,060 | 12/1995 | Gryaznov et al. | 536/24.3 |

FOREIGN PATENT DOCUMENTS

WO9417091 8/1994 WIPO.

OTHER PUBLICATIONS

Giovannangeli et al. PNAS 90: 10013–10017, 1993.
Mayfield et al. Nucleic Acids Research 22: 1909–16, 1994.
Horne and Dervan, J. Am. Chem Soc, 112: 2435–2437, 1990.
Kandimalla et al., *Nucleic Acids Research* 23(21):4510–4517 (1995).
Koh et al., *J. Am. Chem. Soc.* 114:1470 (1992).
Tietze, *Molecular Aspects of Chemotherapy: Proceedings of the Second International Symposium on Molecular Aspects of Chemotherapy*, Chapter 5 (E. Borowski & D. Shugar, Eds. Pergamon Press, 1990).
Zamecnik and Stephenson, *Proc. Natl. Acad. Sci. USA* 75:280–284 (1978).
Agrawal, *Trends in Biotech.* 10:152 (1992).
Cheng and Pettitt, *Proc. Biophys. Molec. Biol.* 58:225 (1992).
Hélène, in *Antisense Res. And Applns.*, pp. 375–385 (Crooke and Lebleu, Eds., CRC Press, Boca Raton, FL, 1993).
Uhlmann and Peyman, *Chem. Rev.* 90:543 (1990).
Thoung et al., *Angew Chem. Int. Ed. Engl.* 32:666 (1993).
Cooney et al., *Science* 241:456 (1988).
Lyamichev et al., *Nucleic Acids Res.* 16:2165 (1988).
Maher et al., *Science* 245:725 (1989).
Moser and Dervan, *Science* 238:645 (1987).

Praseuth et al., *Proc. Natl. Acad. Sci. USA* 85:1349 (1988).
Thoung and Hélène, *Angew. Chem. Int. Ed. Engl.* 32:666 (1993).
Beal and Dervan, *Science* 251:1360 (1991).
Gee et al., *J. Biol. Chem.* 267:11163 (1992).
Postel et al., *Proc. Natl. Acad. Sci. USA* 88:8227 (1991).
Latimer et al., *Nucleic Acids Res.* 22:1549 (1989).
Kibler–Herzog et al., *Nucleic Acids Res.* 18:3545 (1990).
Xodo et al., *J. Molec. Biol.* 19:5625 (1991).
Young et al., *Proc. Natl. Acad. Sci. USA* 88:10023 (1991).
Giovannangeli et al., *J. Am. Chem. Soc.* 113:7775 (1991).
Ono et al., *J. Am. Chem. Soc.* 113:4032 (1991).
Krawczyk et al., *Proc. Natl. Acad. Sci. USA* 89:3761 (1992).
Miller et al., *Biochemistry* 31:6788 (1992).
Koh and Dervan, *J. Am. Chem. Soc.* 114:1470 (1992).
Jetter and Hobbs, *Biochemistry* 32:3249 (1993).
Wang and Kool, *J. Am. Chem. Soc.* 116:885 (1994).
Giovannangeli et al., *Proc. Natl. Acad. Sci. USA* 90:10013 (1993).
Kandimalla and Agrawal, *J. Biomolec. Struc. Dyn.* 10:a086 (1993).
Kandimalla and Agrawal, *Gene* 149:115 (1994).
Kandimalla and Agrawal, *Nucleosides & Nucleotides* 14:991 (1995).
Kandimalla and Agrawal, *Nucleic Acids Res.* 23:1068 (1995).
Kool, *J. Am. Chem. Soc.* 113:6265 (1991).
Prakash and Kool, *J. Am. Chem. Soc.* 114:3523 (1992).
Xodo et al., *Nucleic Acids Res.* 18:3557 (1990).
D'Souza et al., *Biomol. Struct. Dyn.* 10:141 (1991).
Noll et al., *Nucleosides & Nucleotides* 13:997 (1994).

(List continued on next page.)

*Primary Examiner*—W. Gary Jones
*Assistant Examiner*—Dianne Rees
*Attorney, Agent, or Firm*—McDonnell Boehnen Hulbert & Berghoff

[57] ABSTRACT

The present invention provides a novel class of antisense oligonucleotides capable of hybridizing to and inhibiting expression of nucleic acids having mixed purine/pyrimidine sequences by triplex formation. The foldback triplex-forming oligonucleotides (FTFOs) of the invention are comprised of three regions, a duplex-forming region, which is sufficiently complementary to a region of the target nucleic acid to hybridizes to it under the conditions of interest, a triplex-forming region, which is an inverted repeat of the duplex-forming region and folds back upon the duplex formed between the duplex-forming region and the target nucleic acid to form a triplex, and a linker region, which connects the duplex-forming region and the triplex-forming region and allows formation of the triplex. A novel aspect of the FTFOs of the present invention is that from one to five abasic linkers substitute for nucleotides in the triplex-forming region and are positioned to match up with pyrimidine residues of the target when a triplex is formed. This allows the FTFOs of the present invention to target nucleic acid sequences having mixed purine/pyrimidine sequences. FTFOs according to the invention are useful for both in vitro and in vivo modulation of gene expression.

14 Claims, 12 Drawing Sheets

OTHER PUBLICATIONS

De Souza and Kool, *Bioorg. Med. Chem. Lett.* 4:965–970 (1994).
Gryaznov and Lloyd, *Nucleic Acids Res.* 21:5909 (1993).
Perkins et al., *J. Chem. Soc. Chem. Commun.* 3:215 (1993).
Horne and Dervan, *J. Am. Chem. Soc.* 112:2435 (1990).
Jayasena and Johnston, *Biochemistry* 32:2800 (1993).
Xiang et al., *J. Am. Chem. Soc.* 116:11155 (1994).
Mayfield and Miller, *Nucleic Acids Res.* 22:1909 (1994).
Agrawal and Tang, *Antisense Res. Dev.* 2:261 (1992).
Bayever et al., *Antisense Res. Dev.* 3:383 (1993).
Crooke et al., *Clin. Pharm. Therap.* 56:641 (1994).
Zhang et al., *Clin. Pharm. Therap.* 58:44 (1995).
Meyer, in *Methods in Molecular Biology*, vol. 26: Protocols for Oligonucleotide Conjugates, pp. 73–91 (Agrawal, Ed., Humana Press, Totowa, NJ 1994).
Connolly, in *Oligonucleotides and Analogues: A Practical Approach*, pp. 155–183 (Eckstein, Ed., IRL Press, Oxford 1991).
Nelson et al., *Nucleic Acids Res.* 20:6253 (1992).
Storey et al., *Nucleic Acids Res.* 19:4109 (1991).
Robertson et al., *J. Virology* 54:651 (1985).
Harris et al., *J. Virology* 36:659 (1980).
Rice et al., *Science* 229:726 (1985).
Davison and Scott, *J. Gen. Virology* 67:2279 (1986).
Richards et al., *Virology* 89:395 (1978).
Miller and Purcell, *Proc. Natl. Acad. Sci. USA* 87:2057 (1990).
Bukh et al., *Proc. Natl. Acad. Sci. USA* 89:4942 (1992).
Simmonds et al., *J. Gen. Virology* 74:661 (1993).
Collins, in *The Paramyxo Viruses*, Chapter 4, pp. 103–162 (David W. Kingsbury, Ed., 1991).
Campbell et al., *Nature* 311:350 (1984).
Zurita et al., *Proc. Natl. Acad. Sci. USA* 84:2340 (1987).
Stahl and Prusiner, *FASEB J.* 5:2799–2807 (1991).
Ussery and Sindem, *Biochemistry* 32:6206 (1993).
Hélène and Toulmé, *Biochimica et Biophysica Acta* 1049:99 (1990).
Mergny et al., *Biochemistry* 30:9791 (1991).
Raghunathan et al., *Biochemistry* 32:455 (1993).
Smith and Arnott, *Acta Cryst.* vol. 34:3 (1978).
Kyte and Doolittle, *J. Mol. Biol.* 157:105 (1982).
Griffin and Dervan, *Science* 245:967 (1989).
Chothia, *Nature (London)* 248:338 (1974).
Matsumara et al., *Nature* 334:406 (1988).
Agrawal and Sarin, *Advanced Drug Delivery Rev.* 6:251 (1991).

5'-AGA GAG A<u>T</u>G GG<u>T</u> G<u>C</u>G AGA G-3'

| SEQ ID NOs | Complexes | $T_m$ (°C) |
|---|---|---|
| 1 + 16 | T—T—T—3'<br>A—A—A—3'<br>T—T—T—5' | 70.9 |
| 2 + 17 | T—T—X—3'<br>A—A—T—3'<br>T—T—A—5' | 69.4 |
| 3 + 17 | T—T—A—3'<br>A—A—T—3'<br>T—T—A—5' | 68.8 |
| 4 + 18 | T—X—T—3'<br>A—T—A—3'<br>T—A—T—5' | 70.5 |
| 5 + 18 | T—A—T—3'<br>A—T—A—3'<br>T—A—T—5' | 69.1 |
| 6 + 19 | X—T—T—3'<br>T—A—A—3'<br>A—T—T—5' | 70.5 |
| 7 + 19 | A—T—T—3'<br>T—A—A—3'<br>A—T—T—5' | 69.0 |
| 8 + 20 | X—X—X—3'<br>T—A—T—3'<br>A—A—A—5' | 63.0 |
| 9 + 20 | A—A—A—3'<br>T—T—T—3'<br>A—A—A—5' | 61.5 |
| 10 + 20 | T—T—T—3'<br>A—A—A—5' | 61.3 |
| 11 + 21 | T—T—X—3'<br>A—A—C—3'<br>T—T—G—5' | 71.8 |
| 12 + 21 | T—T—G—3'<br>A—A—C—3'<br>T—T—G—5' | 66.4 |
| 13 + 22 | X—X—X—3'<br>T—T—C—3'<br>A—A—G—5' | 67.0 |
| 14 + 22 | A—A—G—3'<br>T—T—C—3'<br>A—A—G—5' | 65.4 |
| 15 + 22 | T—T—C—3'<br>A—A—G—5' | 65.7 |
| 1 + 22 | T—T—T—3'<br>T—T—C—3'<br>T—T—G—5' | 51.2 |
| 8 + 16 | X—X—X—3'<br>A—A—A—3'<br>A—A—A—5' | 54.9 |

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
  ( A ) LENGTH: 43 monomers
  ( B ) TYPE: nucleic acid
  ( C ) STRANDEDNESS: single
  ( D ) TOPOLOGY: linear ( i i i ) HYPOTHETICAL: NO ( i v ) ANTI-SENSE: YES ( x i ) SEQUENCE DESCRIPTION: SEQ ID NO:1:

CTCTCTCTCC CTTCTCTCTC TCTCTCTCTC TTCCCTCTCT CTC          43

( 2 ) INFORMATION FOR SEQ ID NO:2:

( i ) SEQUENCE CHARACTERISTICS:
    ( A ) LENGTH: 43 monomers
    ( B ) TYPE: nucleic acid
    ( C ) STRANDEDNESS: single
    ( D ) TOPOLOGY: linear ( i i i ) HYPOTHETICAL: NO ( i v ) ANTI-SENSE: YES ( x i ) SEQUENCE DESCRIPTION: SEQ ID NO:2:

CTCTCACTCC CTTCTCTCTC TCTCTCTCTC TTCCCTCNCT CTC          43

( 2 ) INFORMATION FOR SEQ ID NO:3:

( i ) SEQUENCE CHARACTERISTICS:
    ( A ) LENGTH: 43 monomers
    ( B ) TYPE: nucleic acid
    ( C ) STRANDEDNESS: single
    ( D ) TOPOLOGY: linear ( i i i ) HYPOTHETICAL: NO ( i v ) ANTI-SENSE: YES ( x i ) SEQUENCE DESCRIPTION: SEQ ID NO:3:

CTCTCACTCC CTTCTCTCTC TCTCTCTCTC TTCCCTCACT CTC          43

( 2 ) INFORMATION FOR SEQ ID NO:4:

( i ) SEQUENCE CHARACTERISTICS:
    ( A ) LENGTH: 43 monomers
    ( B ) TYPE: nucleic acid
    ( C ) STRANDEDNESS: single
    ( D ) TOPOLOGY: linear ( i i i ) HYPOTHETICAL: NO ( i v ) ANTI-SENSE: YES ( x i ) SEQUENCE DESCRIPTION: SEQ ID NO:4:

CTCTCTCACC CTTCTCTCTC TCTCTCTCTC TTCCNCTCT CTC          43

( 2 ) INFORMATION FOR SEQ ID NO:5:

( i ) SEQUENCE CHARACTERISTICS:
    ( A ) LENGTH: 43 monomers
    ( B ) TYPE: nucleic acid
    ( C ) STRANDEDNESS: single
    ( D ) TOPOLOGY: linear ( i i i ) HYPOTHETICAL: NO ( i v ) ANTI-SENSE: YES ( x i ) SEQUENCE DESCRIPTION: SEQ ID NO:5:

CTCTCTCACC CTTCTCTCTC TCTCTCTCTC TTCCCACTCT CTC        43

(2) INFORMATION FOR SEQ ID NO:6:

(i) SEQUENCE CHARACTERISTICS:
        (A) LENGTH: 43 monomers
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO:6:

CTCTCTCTCC CATCTCTCTC TCTCTCTCTC TNCCCTCTCT CTC        43

(2) INFORMATION FOR SEQ ID NO:7:

(i) SEQUENCE CHARACTERISTICS:
        (A) LENGTH: 43 monomers
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO:7:

CTCTCTCTCC CATCTCTCTC TCTCTCTCTC TACCCTCTCT CTC        43

(2) INFORMATION FOR SEQ ID NO:8:

(i) SEQUENCE CHARACTERISTICS:
        (A) LENGTH: 43 monomers
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO:8:

CTCTCACACC CATCTCTCTC TCTCTCTCTC TNCCCNCNCT CTC        43

(2) INFORMATION FOR SEQ ID NO:9:

(i) SEQUENCE CHARACTERISTICS:
        (A) LENGTH: 43 monomers
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO:9:

CTCTCACACC CATCTCTCTC TCTCTCTCTC TACCCACACT CTC        43

(2) INFORMATION FOR SEQ ID NO:10:

(i) SEQUENCE CHARACTERISTICS:
        (A) LENGTH: 24 monomers
        (B) TYPE: nucleic acid
        (C) STRANDEDNESS: single
        (D) TOPOLOGY: linear ( i i i ) HYPOTHETICAL: NO ( i v ) ANTI-SENSE: YES ( x i ) SEQUENCE DESCRIPTION: SEQ ID NO:10:

CTCTCACACC CATCTCTCCC TTCT                                              24

( 2 ) INFORMATION FOR SEQ ID NO:11:

( i ) SEQUENCE CHARACTERISTICS:
        ( A ) LENGTH: 43 monomers
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: YES ( x i ) SEQUENCE DESCRIPTION: SEQ ID NO:11:

CTCTCGCTCC CTTCTCTCTC TCTCTCTCTC TTCCCTCNCT CTC                         43

( 2 ) INFORMATION FOR SEQ ID NO:12:

( i ) SEQUENCE CHARACTERISTICS:
        ( A ) LENGTH: 43 monomers
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: YES ( x i ) SEQUENCE DESCRIPTION: SEQ ID NO:12:

CTCTCGCTCC CTTCTCTCTC TCTCTCTCTC TTCCCTCGCT CTC                         43

( 2 ) INFORMATION FOR SEQ ID NO:13:

( i ) SEQUENCE CHARACTERISTICS:
        ( A ) LENGTH: 43 monomers
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: YES ( x i ) SEQUENCE DESCRIPTION: SEQ ID NO:13:

CTCTCGCACC CATCTCTCTC TCTCTCTCTC TNCCCNCNCT CTC                         43

( 2 ) INFORMATION FOR SEQ ID NO:14:

( i ) SEQUENCE CHARACTERISTICS:
        ( A ) LENGTH: 43 monomers
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: YES ( x i ) SEQUENCE DESCRIPTION: SEQ ID NO:14:

CTCTCGCACC CATCTCTCTC TCTCTCTCTC TACCCACGCT CTC                         43

( 2 ) INFORMATION FOR SEQ ID NO:15:

( i ) SEQUENCE CHARACTERISTICS:

(A) LENGTH: 24 monomers
             (B) TYPE: nucleic acid
             (C) STRANDEDNESS: single
             (D) TOPOLOGY: linear (iii) HYPOTHETICAL: NO (iv) ANTI-SENSE: YES (xi) SEQUENCE DESCRIPTION: SEQ ID NO:15:

CTCTCGCACC CATCTCTCCC TTCT                           24

(2) INFORMATION FOR SEQ ID NO:16:

(i) SEQUENCE CHARACTERISTICS:
             (A) LENGTH: 19 monomers
             (B) TYPE: nucleic acid
             (C) STRANDEDNESS: single
             (D) TOPOLOGY: linear (iii) HYPOTHETICAL: NO (iv) ANTI-SENSE: YES (xi) SEQUENCE DESCRIPTION: SEQ ID NO:16:

AGAGAGAAGG GAGAGAGAG                                 19

(2) INFORMATION FOR SEQ ID NO:17:

(i) SEQUENCE CHARACTERISTICS:
             (A) LENGTH: 19 monomers
             (B) TYPE: nucleic acid
             (C) STRANDEDNESS: single
             (D) TOPOLOGY: linear (iii) HYPOTHETICAL: NO (iv) ANTI-SENSE: YES (xi) SEQUENCE DESCRIPTION: SEQ ID NO:17:

AGAGAGAAGG GAGTGAGAG                                 19

(2) INFORMATION FOR SEQ ID NO:18:

(i) SEQUENCE CHARACTERISTICS:
             (A) LENGTH: 19 monomers
             (B) TYPE: nucleic acid
             (C) STRANDEDNESS: single
             (D) TOPOLOGY: linear (iii) HYPOTHETICAL: NO (iv) ANTI-SENSE: YES (xi) SEQUENCE DESCRIPTION: SEQ ID NO:18:

AGAGAGAAGG GTGAGAGAG                                 19

(2) INFORMATION FOR SEQ ID NO:19:

(i) SEQUENCE CHARACTERISTICS:
             (A) LENGTH: 19 monomers
             (B) TYPE: nucleic acid
             (C) STRANDEDNESS: single
             (D) TOPOLOGY: linear (iii) HYPOTHETICAL: NO (iv) ANTI-SENSE: YES (xi) SEQUENCE DESCRIPTION: SEQ ID NO:19:

AGAGAGATGG GAGAGAGAG                                 19

( 2 ) INFORMATION FOR SEQ ID NO:20:

( i ) SEQUENCE CHARACTERISTICS:
　　　　( A ) LENGTH: 19 monomers
　　　　( B ) TYPE: nucleic acid
　　　　( C ) STRANDEDNESS: single
　　　　( D ) TOPOLOGY: linear ( i i i ) HYPOTHETICAL: NO ( i v ) ANTI-SENSE: YES ( x i ) SEQUENCE DESCRIPTION: SEQ ID NO:20:

AGAGAGATGG GTGTGAGAG                                    19

( 2 ) INFORMATION FOR SEQ ID NO:21:

( i ) SEQUENCE CHARACTERISTICS:
　　　　( A ) LENGTH: 19 monomers
　　　　( B ) TYPE: nucleic acid
　　　　( C ) STRANDEDNESS: single
　　　　( D ) TOPOLOGY: linear ( i i i ) HYPOTHETICAL: NO ( i v ) ANTI-SENSE: YES ( x i ) SEQUENCE DESCRIPTION: SEQ ID NO:21:

AGAGAGAAGG GAGCGAGAG                                    19

( 2 ) INFORMATION FOR SEQ ID NO:22:

( i ) SEQUENCE CHARACTERISTICS:
　　　　( A ) LENGTH: 19 monomers
　　　　( B ) TYPE: nucleic acid
　　　　( C ) STRANDEDNESS: single
　　　　( D ) TOPOLOGY: linear ( i i i ) HYPOTHETICAL: NO ( i v ) ANTI-SENSE: YES ( x i ) SEQUENCE DESCRIPTION: SEQ ID NO:22:

AGAGAGATGG GTGCGAGAG                                    19

TRIPLEX-FORMING ANTISENSE OLIGONUCLEOTIDES HAVING ABASIC LINKERS TARGETING NUCLEIC ACIDS COMPRISING MIXED SEQUENCES OF PURINES AND PYRIMIDINES

BACKGROUND OF THE INVENTION

1. Field of the Invention

This invention relates to the field of antisense oligonucleotides. In particular this invention relates to the field of antisense oligonucleotides useful for inhibiting expression of purine-pyrimidine mixed sequence nucleic acids and methods for their use.

2. Summary of the Related Art

Since Zamecnik and Stephenson, *Proc. Natl. Acad. Sci. USA* 75, 280 (1978) first demonstrated virus replication inhibition by synthetic oligonucleotides, great interest has been generated in oligonucleotides as therapeutic agents. In recent years the development of oligonucleotides as therapeutic agents and as agents of gene expression modulation has gained great momentum. The greatest development has been in the use of so-called antisense oligonucleotides, which form Watson-Crick duplexes with target mRNAs. Agrawal, *Trends in Biotechnology* 10, 152 (1992) extensively reviews the development of antisense oligonucleotides as antiviral agents.

Also important, but somewhat less developed, is the so-called antigene oligonucleotide approach in which oligonucleotides form triplexes with target DNA duplexes through Hoogsteen base pairing. Cheng and Pettitt, *Prog. Biophys. Molec. Biol.* 58, 225 (1992) have recently reviewed developments in this latter approach. See also Hélène in *Antisense Res. and Applns.* pp. 375 (Crooke and Lebleu, Eds., CRC Press, Boca Raton, Fla. 1993); Uhlmann and Peyman, *Chem Rev.* 90, 543 (1990) and Thoung et al., *Angew. Chem Int. Ed. Engl.* 32, 666 (1993). Triplex formation has been observed between DNA and various types of oligonucleotides. Polypurine and polypyrimidine sequences form Py.Pu:Py or Pu.Pu:Py triple helices (where ":" indicates Watson-Crick bonding and "." indicates Hoogsteen bonding). Cooney et al., *Science* 241, 456 (1988); Lyamichev et al., *Nucleic Acids Res.* 16, 2165 (1988); Maher et al., *Science* 245, 725 (1989); Moser & Dervan, *Science* 238, 645 (1987); Peuth et al., *Proc. Natl. Acad. Sci. USA* 85, 1349 (1988). In a triple helix, an oligonucleoticle third strand binds to the polypurine sequence in the major groove of the polypurine:polypyrimidine double helix, forming Hoogsteen hydrogen bonds with the purine target strand in either parallel or antiparallel orientation. Cheng and Pettitt, supra and Thoung & Hélène, *Angew. Chem. Int. Ed. Engl.* 32, 666 (1993). In general, polypyrimidine oligonucleotides bind through T.A:T and pH-dependent C+.G:C triplet formation by Hoogsteen (in parallel orientation) or reverse Hoogsteen (in antiparallel orientation) hydrogen bonding. Thoung & Helene, supra. In contrast, polypurines bind only in antiparallel orientation through G.G:C or A.A:T triplet formation in a pH-independent manner (Beal & Dervan, *Science* 251, 1360 (1991); Gee et al., *J. Biol. Chem.* 267, 11163 (1992); Postel et al., *Proc. Natl. Acad. Sci. USA* 88, 8227 (1991). G.G:C and A.A:T triplets are much weaker than Py.Pu:Py triplets.

Cooney et al., *Science* 241, 456 (1988) teaches triplex formation between DNA and an oligodeoxynucleotide phosphodiester. Latimer et al., *Nucleic Acids Res.* 22, 1549 (1989) discloses triplex formation involving oligodeoxynucleotide phosphorothioates. Kibler-Herzog et al., *Nucleic Acids Res.* 18, 3545 (1990) discloses triplex formation involving short oligodeoxynucleotide methylphosphonates. Various base modifications that enhance triplex formation are also known, including C5-methylation of cytosine (Xodo et al., *J. Molec. Biol.* 19, 5625 (1991)), use of the bicyclic cytosine analog, MODA (Young et al., *Proc. Natl. Acad. Sci. USA* 88, 10023 (1991)), and use of a synthetic α-anomeric nucleotide (Praseuth et al., *Proc. Natl. Acad. Sci. USA* 85, 1349 (1988)). Giovannangeli et al., *J. Am. Chem. Soc.* 113, 7775 (1991) teaches that attachment of an acridine intercalator onto the 5'-end of a capped oligonucleotide also enhances triplex stability. Oligonucleotide-mediated triplex formation can cause inhibition of transcription, at least in vitro (see Cooney et al. and Young et al., supra).

Requirement of acidic pH conditions and limited base recognition are impediments to full implementation of the triple helix approach. Several modified bases (Ono et al., *J. Am. Chem. Soc.* 113, 4032 (1991); Krawczyk et al., *Proc. Natl. Acad. Sci. U.S.A.* 89, 3761 (1992); Miller et al., *Biochemistry* 31, 6788 (1992); Koh et al., *J. Am. Chem. Soc.* 114, 1470 (1992); and Jetter and Hobbs, *Biochemistry* 32, 3249 (1993) or alternate designs have been reported to overcome these problems, but with limited success. Recently, an alternate approach for targeting single stranded homopyrimidine sites using circular oligonucleotides through G.G:C and T.A:T kind of triple helix formation has been proposed in which the third strand binds antiparallel to the purine strand through reverse Hoogsteen hydrogen bonding. Wang and Kool, *J. Am. Chem. Soc.* 116, 885 (1994).

To improve the specificity and affinity of antisense oligonucleotides, several groups have designed oligonucleotides that can bind to single-stranded nucleic acids (DNA and RNA) by forming a triplex in the Py.Pu:Py motif. (Giovannangeli et al., *J. Am. Chem. Soc.*, supra; Giovannangeli et al., *Proc. Natl. Acad. Sci. USA* 90, 10013 (1993); Kandimalla and Agrawal, *J. Biomolec. Struct. Dyn.* 10, aO86 (1993); Kandimalla and Agrawal, *Gene* 149, 115 (1994); Kandimalla and Agrawal, *Nucleosides and Nucleotides* 14, 991; Kandimalla and Agrawal, *Nucleic Acids Res.* 23, 1068 (1995); Kool, *J. Am. Chem. Soc.* 113, 6265 (1991); Prakash & Kool, *J. Am. Chem. Soc.* 114, 3523 (1992); Xodo et al., *Nucleic Acids Res.* 18, 3557 (1990). These oligonucleotides have been called foldback triplex-fomiing oligonucleotides (FTFOs), analogous with triplex-forming oligonucleotides (TFOs) that bind to duplex DNA. Kandimalla & Agrawal, *Gene*, supra. The FTFOs bind to single-stranded targets with increased affinity and greater specificity than conventional antisense oligonucleotides and TFOs. FTFOs require acidic pH conditions, however, if cytosines are involved in the formation of the triplex and the target sites are polypurines, as is the case with TFOs.

In recent years several groups reported circular or foldback triplex formation at homopurine single-stranded sites using linear (Kandimalla and Agrawal, *Gene*, supra; Xodo et al., *Nucleic Acids Res.*, supra; D'Souza et al., *Biomol. Struct. Dyn.* 10, 141 (1992); Noll et al., *Nucleosides Nucleotides* 13, 997 (1994)), circular (Kool, *J. Am. Chem. Soc.*, supra; Prakash and Kool, *J. Am. Chem. Soc.*, supra; and D'Souza and D. J.; Kool, *Bioorg. Med. Chem. Lett.* 4, 965 (1994)), and ligand conjugated linear (Giovannangeli et al., *J. Am. Chem. Soc.*, supra; Giovannangeli, *Proc. Natl. Acad. Sci. USA*, supra; and Gryaznov and Lloyd, *Nucleic Acids Res.* 21, 5909 (1993)) homopyrimidine oligonucleotides, which may be useful as agents for gene expression control at translation level by targeting mRNA. The linear oligonucleotides that form foldback triplexes with a purine strand were shown to disrupt guanine quadruplex structures if the target site contains such quadruplex forming base sequences. Kandimalla and Agrawal, *Nucleic Acids Res.*, supra. These oligonucleotides were demonstrated to bind at purine sites of a double helical DNA through strand invasion mechanism by D-loop formation. Perkins et al., *J. Chem. Soc., Chem. Commun.* 215 (1993).

Two difficulties unique to the triplex approach are the pH-dependence of $C^+.G:C$ triplex formation and the fact that their target sites are restricted to homopurines. Several alternate designs (Horne & Dervan, *J. Am. Chem. Soc.* 112, 2435 (1990); Jayasena & Johnston, *Biochemistry* 32, 2800 (1993); Ono, et al., *J. Am. Chem. Soc.* 113, 4032 (1991) and modified bases (Jetter & Hobbs, *Biochemistry* 32, 3249 (1993); Koh & Dervan, *J. Am. Chem. Soc.* 114, 1470 (1992); Miller et al., *Biochemistry* 31, 6788 (1992); Ono et al., supra; Xiang et al., *J. Am. Chem. Soc.* 116, 11155 (1994); Young, et al., *Proc. Natl. Acad. Sci. USA*, supra) have been proposed to overcome these problems, but with limited success.

In order to target pyrimidine base containing sequences, Horne and Dervan, supra, have incorporated a null residue (1,2-dideoxyo-D-ribose) in oligonucleotides opposite the Py:Pu base pairs. The oligonucleotide skips a pyrimidine base in a purine-rich target sequence. The authors concluded that a pyrimidine third strand containing this abasic (null) site was significantly less stable than the triplets T.A:T, $C^+.G:C$, and G.T:A, and the decrease in binding produced by an abasic residue was similar to that observed with imperfectly matched natural base triplets. Recently, a similar approach has been reported using 2-aminobutyl-1,3-propanediol linker for TFOs in Pu.Pu:Py motif. Mayfield and Miller, *Nucleic Acids Res.* 22, 1909 (1994). These authors reported that a propanediol linker may be used to skip over pyramidinc interruptions in a target sequence, thereby stabilizing the triplex, but at the expense of sequence specificity. The increased triplex stabilization by propanediol-containing TFOs did not result in increased inhibition of Spl binding to the Ha-ras promoter. The utility of this linker in the Py.Pu:Py motif, however, and its affinity against C:G and T:A base pairs with respect to mismatched bases has not been studied.

Both the antisense and antigene oligonucleotide approaches have as their goal gene expression modulation that is beneficial in understanding gene expression and in therapeutic treatment of diseases or conditions involving gene expression. Antisense oligonucleotides, which bind to single-stranded mRNA to form a double helix and thereby control gene expression have been advanced to human clinical trials. Agrawal & Tang, *Antisense Res. Dev.* 2,261 (1992); Bayever et al., *Antisense Res. Dev.* 3, 383 (1993); Crook et al., *Clin. Pharm. Therap.* 56, 641 (1994); Zhang et al. *Clin. Pharm. Therap.* 58, 44 (1995). Two major characteristics of oligonucleotide compounds that are well suited to meet these goals are high specificity and an ability to interfere with gene expression upon binding. Enhancement of these characteristics is always desirable. There is a need, therefore, for new oligonucleotide compounds having even greater specificity and more stable complex formation (leading to increased ability to interfere with gene expression) than existing compounds. In particular, there is a need for antisense oligonucleotides capable of targeting and inhibiting nucleic acids comprising sequences having both purine and pyrimidine nucleotides.

SUMMARY OF THE INVENTION

The present invention comprises antisense oligonucleotides that target and inhibit the expression of nucleic acids having mixed purine and pyrimidine sequences. In particular, the present invention provides foldback triplex-forming oligonucleotides (FTFOs) comprising sequences in which one or more nucleotides are replaced with an abasic moiety, i.e., a moiety without a base.

The FTFOs of the present invention comprise a duplex-forming region, a triplex-forming region, and a linker region. The duplex-forming region hybridizes to the target nucleic acid through normal Watson-Crick bonding and the triplex-forming region folds back upon the duplex thereby formed to form a triplex by Hoogsteen bonding to the duplex. Typically, hybridization of the third strand (be it either a complex of three separate nucleic acid strands or the foldback triplex-forming approach) is to a homopurine region of one of the stands involved in the Watson-Crick duplex. Accordingly, art recognized FTFOs generally target homopurine sequences only. The FTFOs of the present invention, however, can target polypurine sequences having several interspersed pyrimidine nucleotides. Hence, FTFOs of the present invention broaden the range of nucleic acids that can be targeted for inhibition. They accomplish this by including in the triplex-forming region one or more abasic linkers positioned such that, during triplex formation, the abasic linkers match up against the interspersed pyrimidine nucleotide of the target nucleic acid, thereby resulting in the triplex-forming region "skipping over" the pyrimidine nucleotide as Hoogsteen-type hydrogen bonds are formed.

The duplex forming region of the foldback triplex-forming oligonucleotides of the present invention is sufficiently complementary to the target nucleic acid (in the Watson-Crick sense) to hybridize to the target under the conditions (e.g., pH and temperature) of interest. The triplex-forming region is complementary (in the Hoogsteen sense) to the duplex forming region, being the mirror image of the duplex forming region, except that from one to five nucleotides are replaced with an abasic linker that is matched against a pyrimidine base of the Watson-Crick substituent lacking a base abasic linker is a substituent lacking a base and is positioned within the triplex-forming region so as to match up with a pyrimidine in the target sequence upon triplex formation. The linker region connects the duplex-forming region and the triplex-forming region, allowing the oligonucleotide to fold upon itself, and comprises, for example, a short nucleotide sequence (e.g., a pentanucleotide) or some other non-nucleotide substituent such as ethylene glycol.

The number of abasic linkers that are incorporated into the oligonucleotides of the invention depends on the length of the triplex-forming region. The longer the triplex forming region, the more abasic linkers that can be incorporated. When the triplex-forming region is short (e.g., about 10 nucleotides in length), only one or two abasic linkers can be incorporated and still maintain the triplex-forming ability of the oligonucleotide. When the triplex-forming region is long (about 30 nucleotides or more), 4 or 5 abasic linkers can be used.

Foldback triplex-forming oligonucleotides of the present invention are useful tools for gene modulation and have both in vitro and in vivo utilities. Because FTFOs of the present invention can inhibit gene expression, in vitro they can be used as a convenient alternative to the laborious technique of deletion mutation for the determination of gene function. The importance of this use is easily appreciated when one realizes that the biological function of most known genes was determined by deletion mutation.

In vivo, the foldback triplex-forming oligonucleotides of the present invention are therapeutically useful for treating a wide variety of maladies ranging from pathogen caused diseases to aberrant expression of endogenous nucleic acids. By targeting the pathogenic or aberrant nucleic acid, administration of the foldback triplex-forming oligonucleotides of the present invention can inhibit expression of the nucleic acid, thereby preventing further adverse effects.

The foregoing merely summarizes certain aspects of the present invention and is not intended, nor should it be construed, as limiting the invention in any manner. All patents and publications cited herein establish the state of the art and are hereby incorporated by reference in their entirety.

BRIEF DESCRIPTION OF THE DRAWINGS

FIG. 12 displays the results of the UV thermal melting studies of Example 2. Specific bases under study are show; X represents the 2-aminobutyl-1,3-propanediol abasic linker.

DETAILED DESCRIPTION OF THE PREFERRED EMBODIMENTS

Figures 1A, 1B:
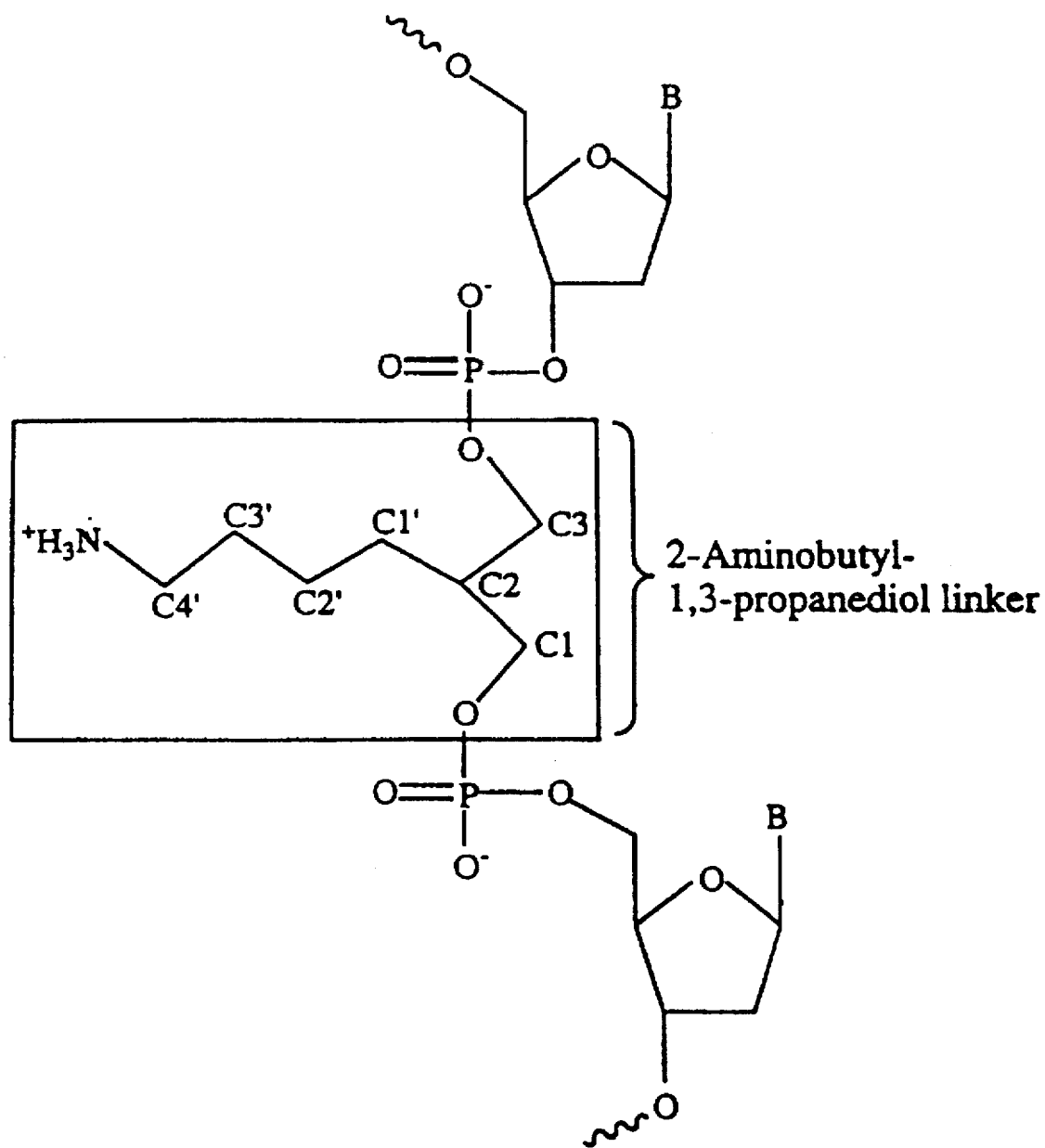
FIG. 1A displays the structure of the 2-aminobutyl-1,3-propanediol (abasic) linker.
FIG. 1B displays a typical purine-rich target sequence in which the pyrimidine bases are indicated in bold and underlined.

The present invention comprises antisense oligonucleotides that target and inhibit the expression of nucleic acids having mixed purine and pyrimidine sequences. In particular, the present invention provides foldback triplex-forming oligonucleotides (FTFOs) comprising sequences in which one or more nucleotides are replaced with an abasic moiety, i.e., a moiety without a base.

In the absence of established natural or modified bases that can form Hoogsteen base pairs with pyrimidine bases in the target strand for triplex formation, we substituted an abasic linker as a "null site" in the Hoogsteen domain of the FTFOs. As used herein, the term "null site" means a site within an oligonucleotide comprising an "abasic linker;" the term "abasic linker" means a moiety that substitutes for a nucleotide within an oligonucleotide but has no base. This null site matches up against 1-3 pyrimidine bases in the target sequence to overcome the limitation of target sites to polypurines in triplex formation. The linker 2-aminobutyl-1,3-propanediol [2-(4-amino-butyr-1-yl)-1,3-propanediol] (FIG. 1A), for example, maintains normal phosphodiester linkage distance and permits the oligonucleotide to target pyrimidine bases. At the same time, the specificity of the FTFOs according to the invention is maintained by Watson-Crick complementary recognition of the target strand, which does not occur in the case of TFOs (which hybridize to duplex nucleic acid through Hoogsteen bond formation only).

Complementary base recognition through Watson-Crick duplex and Hoogsteen triplex formation is highly sequence-specific. The foldback and circular oligonucleotides that bind to the single-stranded target sequence are much more sequence-specific than oligonucleotides that bind to the target by either Watson-Crick hydrogen bonding (antisense) or Hoogsteen hydrogen bonding (antigene or triplex-forming oligonucleotides) alone. These FTFOs are more sequence-specific because they read the target sequence twice, first when they form a duplex with the target sequence, and second when the Hoogsteen domain binds to form the triplex. Kandimalla & Agrawal, Gene, supra; Prakash & Kool, J. Am. Chem. Soc., supra. An abasic site introduced into a TFO intended to bind to double-stranded DNA containing pyrimidine interruptions can decrease the sequence-specificity by allowing the TFO to bind to non-targeted sequences. Horne & Dervan, Nucleic Acids Res., supra; Mayfield & Miller, Nucleic Acids Res., supra. This problem does not occur with FTFOs that contain abasic sites in the Hoogsteen domain, because sequence-specificity is mainly determined by the Watson-Crick domain, while the Hoogsteen strand contributes to the stability of the resulting foldback triplex complex only after the initial duplex is formed.

Foldback triplex-forming oligonucleotides according to the invention generally have at least three structural features, a duplex-forming region, a triplex-forming region, and a linker region. For the intact foldback triplex-forming oligonucleotides and the various structural regions referred to herein, except where explicitly stated otherwise, structural features include, but are not limited to, having polymers of 5' to 3' linked ribonucleosides, 2' substituted ribonucleosides and/or deoxyribonucleotides. Internucleotide linkages may be natural phosphodiester linkages or an artificial linkages, such as phosphorothioates, phosphorodithioates, phosphoramidates, alkylphosphonates, alkylphosphonothioates, sulfonates, carbamates and/or phosphotriester linkages. See, e.g., Uhlmann and Peyman, supra. Moreover, such oligonucleotides encompass oligo-nucleotides having modifications on the bases (see, e.g., Meyer in *Methods in Molecular Biology*, Vol. 26: *Protocols for Oligonucleotide Conjugates* pp. 73-91 (Agrawal, Ed., Humana Press, Totowa, N.J. 1994); and Connolly in *Oligonucleotides and Analogues: A Practical Approach* pp. 155–183 (Eckstein, Ed., IRL Press, Oxford 1991) and/or sugar residues (e.g., 2'-O methylation) as well as those having nuclease-resistance conferring substituents or bulky substituents at the 3' and/or 5' end.

The duplex-forming region of a foldback triplex-forming oligonucleotide of the present invention is characterized by having a nucleotide sequence that is sufficiently complementary to a target nucleic acid sequence to hybridize to the target nucleic acid sequence under experimental or physiological conditions. In a preferred embodiment, the duplex forming region sequence is exactly complementary (in the Watson-Crick sense) to the target nucleic acid. Preferably, the duplex-forming region has from about 8 to 50 nucleotides, and most preferably has from about 12 to about 35 nucleotides. The target nucleic acid can, for experimental purposes, have essentially any nucleotide sequence. For therapeutic or medical uses of foldback triplex-forming oligonucleotides, however, the duplex-forming region will preferably have a nucleotide sequence that is sufficiently complementary to hybridize under physiological conditions to the nucleotide sequence of a nucleic acid that is involved in a particular disease state or physiological condition.

The triplex-forming region of a foldback triplex-forming oligonucleotide is characterized by having a nucleotide sequence that is the mirror image of the duplex-forming region, thus forming a palindrome with all or part of the duplex-forming region. Put differently, the base sequence of the triplex-forming region is an inverted repeat of all or a portion of the duplex-forming region of the same foldback triplex-forming oligonucleotide (and thus an inverted complement of the target sequence), not taking into account any base modifications. In addition, the triplex forming region has one to five abasic linkers. The triplex-forming region preferably has at least about 8 monomers comprising nucleotides and abasic linkers and can have any number of monomers up to the full length of the duplex-forming region. In a preferred embodiment, the nucleotide bases of the triplex-forming region include 5-bromodeoxyuridine and/or 5-methyl-cytosine, each of which promote Hoogsteen base pairing at or near physiological pH. The bicyclic cytosine analog MODA, α-anomeric nucleotides and/or terminal acridines, other terminal intercalators, or DNA cutting or modifying agents such as EDTA-FeII, and cc-1065, or hydrophobic or amphophilic groups such as cholesterol, cyclodextrins, or polyamines may also be present in the triplex (or duplex) forming region to promote triplex stability or target nucleic acid destruction.

The number of abasic linkers that are incorporated into the oligonucleotides of the invention depends on the length of the triplex-forming region. The longer the triplex forming region, the more abasic linkers that can be incorporated. When the triplex-forming region is short (e.g., about 10 nucleotides in length), only one or two abasic linkers can be incorporated and still maintain the triplex-forming ability of the oligonucleotide. When the triplex-forming region is long (about 30 nucleotides or more), 4 or 5 abasic linkers can be used. The number of abasic linkers incorporated into an oligonucleotide according to the invention is dependent on the stability of the resulting triplex formed with the target. As many abasic linkers can be incorporated as can maintain a melting temperature of about 50° C. or more.

The linker region of foldback triplex-forming oligonucleotides is a flexible region that connects the duplex-forming region and the triplex-forming region. The linker region may be an oligonucleotide having from about 3 to about 10 nucleotides. In a preferred embodiment, the linker region is an oligonucleotide having about 5 nucleotides. Alternatively, the linker region can be some other flexible chemical structure, such as a substituted or unsubstituted alkyl or aryl group having about 4 to 20 carbon atoms (e.g., isopropyl, o-xylyl), or a ribose or 1',2'-dideoxyribose chain having from 1 to about 3 monomers. In a preferred embodiment, the linker region is hexaethylene glycol. At a minimum, the linker region is a single covalent bond.

Figure 11:
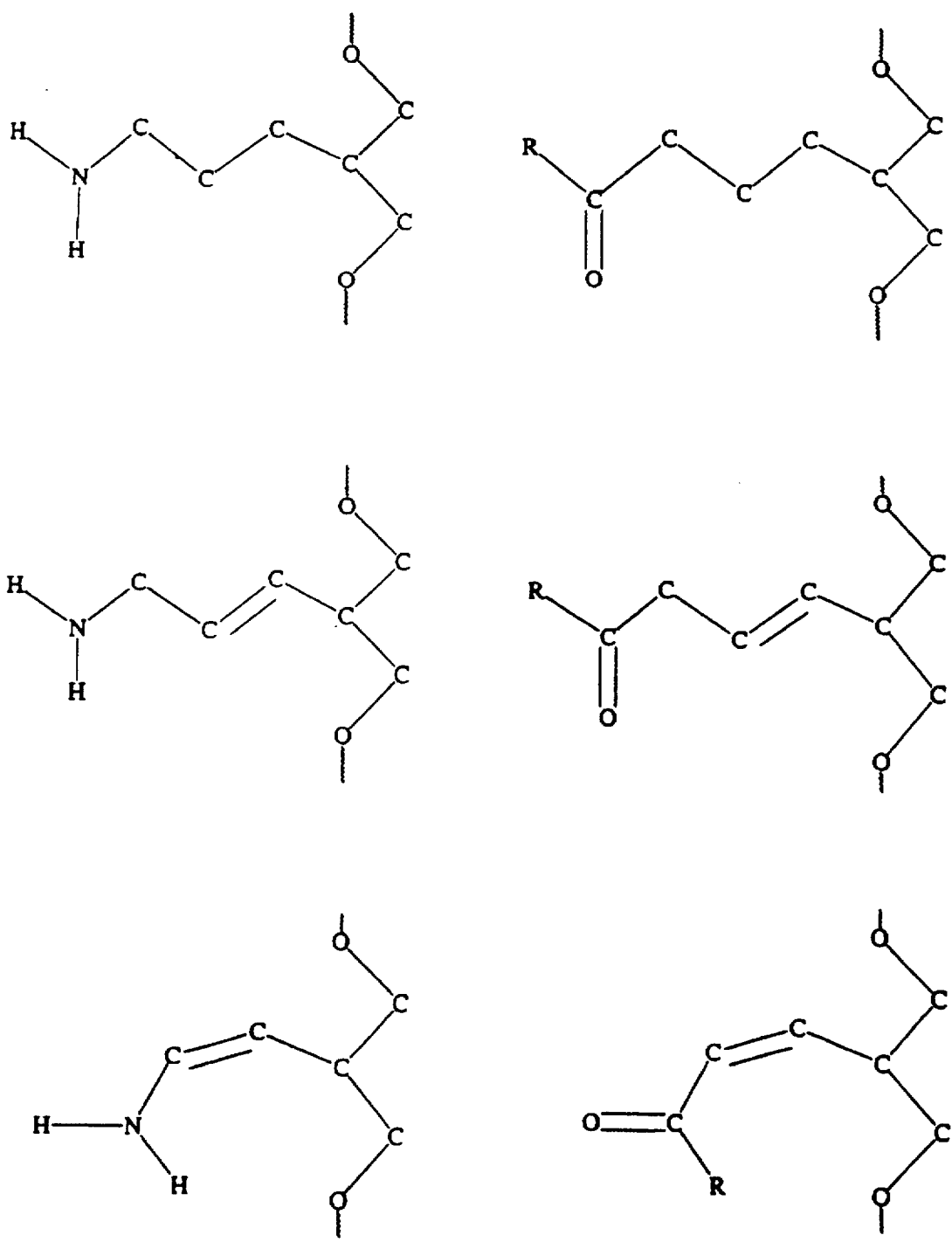
FIG. 11 displays the abasic linkers of the present invention, wherein R represents a hydrogen, hydroxyl, alkyl, or amino group.

The experiments and molecular modeling described herein demonstrate that suitable abasic linkers for use in the present invention are 2-substituted propylene glycols having the structure:

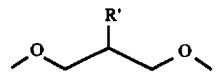

where R' is $NH_2(CH_2)_4-$, $NH_2(CH_2)_3-$, $NH_2CH_2CH=CH-$, $NH_2CH=CH-$, $RCO(CH_3)_2-$, $RCOCH_2CH=CH-$, $RCOCH=CH-$, wherein R is $-H$, $-OH$, $-NH_2$, $-CH_3$, or $-C_2H_3$. See also FIG. 11. In a preferred embodiment, R' is $NH_2(CH_2)_4-$.

Foldback triplex-forming olgionucleotides according to the invention can be synthesized using reported methodologies (Agrawal, *Methods in Molecular Biology*, Vol. 26, *Protocols for Oligonucleotide Conjugates*, (Agrawal, Ed., Humana Press, Totowa, N.J. 1994). Nelson et al., *Nucleic Acids Res.* 20, 6253 (1992) describe synthesis of abasic linker structures. For foldback triplex-forming oligonucleotides containing non-oligonucleotide linker regions, synthesis can still be carried out according to these procedures, provided that all hydroxyl groups are first protected by an appropriate protecting group, such as a dimethoxytrityl group, that all amino groups present be protected by an appropriate protective group, such as a trifluoroacetyl group, and that one end be linked to an appropriate coupling group, such as a β-cyanoethyl-phosphoramidite or H-phosphonate group.

Foldback triplex-forming oligonucleotides according to the invention are useful for a variety of purposes. First, they are useful for in vitro studies of nucleic acid triplex formation. In a foldback triplex-forming oligonucleotide it is possible to vary many parameters, such as internucleotide linkage types, base modifications, linker length and flexibility, etc. to study the kinetics of triplex formation and disruption, which may be a biologically important process.

In addition, foldback triplex-forming oligonucleotides can be used in place of traditional antisense oligonucleotides in tissue culture and animal models for studying gene expression. In these systems, the increased specificity and complex stability of foldback triplex-forming oligonucleotides is beneficial, enhancing nucleic acid expression inhibition. The foldback triplex forming olgionucleotides according to the invention provide an attractive alternative to the laborious technique of deletion mutation in the modulation of gene expression for the in vitro or in vivo determination of the role of the targeted gone in biological processes.

Finally, foldback triplex-forming oligonucleotides are useful as therapeutic agents for diseases or physiological conditions involving expression of specific genes. The disease or condition that a particular foldback triplex-forming oligonucleotide is useful for treating will depend upon the nucleotide sequence to which the duplex-forming region is sufficiently complementary to hybridize under physiological conditions. In many cases the nucleic acid sequence will be a viral nucleic acid sequence. The use of antisense oligonucleotides to inhibit various viruses is well known, and has recently been reviewed in Agrawal, *Trends in Biotech.* 10, 152–158 (1992). The lessons learned from antiviral antisense oligonucleotides can be applied to duplex-forming regions. Viral nucleic acid sequences that hybridize to effective antisense oligonucleotides have been described for many viruses, including human immunodeficiency virus type 1 (U.S. Pat. No. 4,806,463), Herpes simplex virus (U.S. Pat. No. 4,689,320), Influenza virus (U.S. Pat. No. 5,194,428) and Human papilloma virus (Storey et al., *Nucleic Acids Res.* 19, 4109 (1991)). Sequences hybridizing to any of these nucleic acid sequences can be used for the duplex-forming region of foldback triplex-forming oligonucleotides, as can nucleotide sequences complementary to nucleic acid sequences from any other virus. Additional viruses that have known nucleic acid sequences against which foldback triplex-forming oligonucleotides can be prepared include, but are not limited to, Foot and Mouth Disease Virus (See Robertson et al., *J. Virology* 54, 651 (1985); Harris et al., *J. Virology* 36, 659 (1980)), Yellow Fever Virus (See Rice et al., *Science* 229, 726 (1985)), Varicella-Zoster Virus (See Davison and Scott, J. Gen. Virology 67, 2279 (1986), Cucumber Mosaic Virus (See Richards et al., *Virology* 89, 395 (1978)), Hepatitis B Virus (See Raney and McLachlen, in *Molecular Biology of Hepatitis B Virus* (CRC Press, 1991)), Hepatitis C Virus (See Miller and Purcell, *Proc. Natl. Acad. Sci. USA* 87, 2057 (1990); *Proc. Natl. Acad. Sci. USA* 89, 4942 (1992); *J. General Virology* 74, 661 (1993)), and Respitory Syncitial Virus (See Collins, in *The Paramyxo Viruses*, Chapter 4, pp. 103–162 (David W. Kingsbury, Ed., 1991)).

Alternatively, the duplex-forming region can have a nucleotide sequence complementary to a nucleic acid sequence of a pathogenic organism. The nucleic acid sequences of many pathogenic organisms have been described, including the malaria organism, *Plasmodium falciparum*, and many pathogenic bacteria. Nucleotide sequences hybridizing to nucleic acid sequences from any such pathogenic organism can form the duplex-forming region of foldback triplex-forming oligonucleotides. Examples of pathogenic eukaryotes having known nucleic acid sequences against which foldback triplex-forming oligonucleotides can be prepared include, but are not limited to *Trypanosoma brucei gambiense* and Leishmania (See Campbell et al., *Nature* 311, 350 (1984)), and *Fasciola hepatica* (See Zurita et al., *Proc. Natl. Acad. Sci. USA* 84, 2340 (1987)).

Antifungal foldback triplex-forming oligonucleotides can be prepared using a duplex-forming region having a nucleotide sequence that is complementary to a nucleic acid sequence from, e.g., the chitin synthetase gene, and antibacterial foldback triplex-forming oligonucleotides can be prepared to have a duplex-forming region complementary to, e.g., the alanine racemase gene.

In yet another embodiment, the duplex-forming region of foldback triplex-forming oligonucleotides can have a nucleotide sequence complementary to a cellular gene or gene transcript, the abnormal expression or product of which results in a disease state. The nucleic acid sequences of several such cellular genes have been described, including the prion protein (Stahl and Prusiner, *FASEB J.* 5, 2799–2807 (1991)), the amyloid-like protein associated with Alzheimer's disease (U.S. Pat. No. 5,015,570), and various well-known oncogenes and proto-oncogenes, such as c-myb, c-myc, c-abl, and n-ras. In addition, oligonucleotides that inhibit the synthesis of structural proteins or enzymes involved largely or exclusively in spermatogenesis, sperm motility, the binding of the sperm to the egg or any other step affecting sperm viability may be used as contraceptives for men. Similarly, contraceptives for women may be oligonucleotides that inhibit proteins or enzymes involved in ovulation, fertilization, implantation or in the biosynthesis of hormones involved in those processes. Hypertension can be controlled by oligonucleotides that suppress the synthesis of angiotensin-converting enzyme or related enzymes in the renin/angiotensin system. Platelet aggregation can be controlled by suppression of the synthesis of enzymes necessary for the synthesis of thromboxane A2 for use in myocardial and cerebral circulatory disorders, infarcts, arteriosclerosis, embolism and thrombosis. Deposition of cholesterol in arterial wall can be inhibited by suppression of the synthesis of fatty acyl co-enzyme A: cholesterol acyl transferase in arteriosclerosis; inhibition of the synthesis of cholinephosphotransferase may be useful in hypolipidemia.

There are numerous neural disorders in which foldback triplex-forming oligonucleotides can be used to reduce or eliminate adverse effects of the disorder. For example, suppression of the synthesis of monoamine oxidase can be used in Parkinson's disease. Suppression of catechol O-methyl transferase can be used to treat depression. Suppression of indole N-methyl transferase can be used in treating schizophrenia.

Suppression of selected enzymes in the arachidonic acid cascade which leads to prostaglandins and leukotrienes may be useful in the control of platelet aggregation, allergy, inflammation, pain and asthma.

Suppression of the protein expressed by the multi-drug resistance (mdr) gene, which is responsible for development of resistance to a variety of anti-cancer drugs and is a major impediment in chemotherapy may prove to be beneficial in the treatment of cancer.

Nucleotide sequences complementary to nucleic acid sequences from any of these genes can be used for the duplex-forming region of foldback triplex-forming oligonucleotides according to the invention, as can be oligonucleotide sequences complementary to any other cellular gene or gene transcript, the abnormal expression or product of which results in a disease state. Antisense regulation of gene expression in plant cells has been described in U.S. Pat. No. 5,107,065. Since the nucleotide sequence of the duplex-forming region can be adapted to form Watson-Crick base pairs with essentially any gene, the therapeutic spectrum of foldback triplex-forming oligonucleotides should be very broad. Still, certain diseases are of particular interest. For example, a variety of viral diseases may be treated by foldback triplex-forming oligonucleotides, including AIDS, ARC, oral or genital herpes, papilloma warts, flu, foot and mouth disease, yellow fever, chicken pox, shingles, HTLV-leukemia, and hepatitis. Among fungal diseases treatable by foldback triplex-forming oligonucleotides are candidiasis, histoplasmosis, cryptococcocis, blastomycosis, aspergillosis, sporotrichosis, chromomycosis, dematophytosis and coccidioidomycosis. The method can also be used to treat rickettsial diseases (e.g., typhus, Rocky Mountain spotted fever), as well as sexually transmitted diseases caused by *Chlamydia trachomatis* or *Lymlphogranuloma venereum*. A variety of parasitic diseases can be treated by foldback triplex-forming oligonucleotides including amebiasis, Chagas' disease, toxoplasmosis, pneumocystosis, giardiasis, cryptosporidiosis, trichomoniasis, *Pneumocystis carini* pneumonia as well as worm (helminthic) diseases such as ascariasis, filariasis, trichinosis, schistosomiasis and nematode or cestode infections. Malaria can be treated by foldback triplex-forming oligonucleotides regardless of whether it is caused by *P. falciparum, P. vivax, P. orale,* or *P. malariae.* The infectious diseases identified above can all be treated by foldback triplex-forming oligonucleotides because the infectious agents for these diseases are known and thus foldback triplex-forming oligonucleotides according to the invention can be prepared having a target-forming region with a nucleotide sequence that hybridizes to a nucleic acid sequence essential for the propagation of the infectious agent, e.g., an essential gene if a suitable target region susceptible to antisense inhibition can be identified.

Because DNA can breathe (see, e.g., Ussery and Sindem, *Biochemistry* 32, 6206 (1993)), foldback triplex-forming oligonucleotides can form triplexes with DNA. See, e.g., Hélène and Toulmé, *Biochimica et Biophysica Acta* 1049, 99 (1990) at page 100.

Cancer cells have a much lower pH than normal cells. See, e.g., Lutz F. Tietze in *Molecular Aspects of Chemotherapy: Proceedings of the Second International Symposium on Molecular Aspects of Chemotherapy,* Chapter 5 (E. Borowski and D. Shugar, Eds., Pergamon Press, 1990). Accordingly, one can design foldback triplex-forming oligonucleotides that are capable of forming foldback triplexes in cancer cells preferentially. Oligonucleotide activity in cancer cells can be obtained by designing foldback triplex-forming oligonucleotides to contain more cytosines than thymine, because cytosine must be protonated, preferably at low pH, to form Hoogsteen bonds. It is this difference that provides the opportunity to design foldback triplex-forming oligonucleotides that preferentially form foldback triplexes in cancer cells only. For normal cells, methylcytosines, which can be protonated near physiological pH (6.5–6.8), can be used.

The following Examples are provided for illustrative purposes only and are not intended, nor should they be construed, as limiting the invention in any manner.

EXAMPLES

Example 1

Oligonucleotide Synthesis and Purification

Oligodeoxyribonucleotides were synthesized on a Milligen 8700 DNA synthesizer using cyanoethyl phosphoramidite chemistry. All the monomer synthons were obtained from Milligen (Bedford, Mass.). The other solvents and reagents required for the synthesis were purchased from either Milligen or Cruachem (Livingstone, United Kingdom). The oligonucleotides containing the abasic linker were synthesized on a DNA synthesizer using N-Fmoc-O$^1$-DMT-O$^3$-cyano-ethoxydiisopropylaminophosphinyl-2-aminobutyryl-1,3-propanediol that was purchased from Clontech (Palo Alto, Calif.). The oligonucleotides were deprotected by incubating with concentrated ammonium hydroxide at room temperature for 1.5 hrs and then incubating the supernatant at 55° C. for 6 hrs. Oligonucleotides were then purified on a C$_{18}$ reverse-phase HPLC, using 0.1M aqueous ammonium acetate and acetonitrile containing a 20% 0.1M ammonium acetate solvent system. HPLC-purified oligonucleotides were detritylated with 80% aqueous acetic acid for 1 hr at room temperature. The oligonucleotides were desalted on C$_{18}$ reverse-phase sep-pack cartridges (Waters, Milford, Mass.) and the purity was checked by polyacrylamide gel electrophoresis (PAGE). Oligonucleotides that were less than 95–97% pure were further purified by preparative 15% PAGE.

Figure 2:
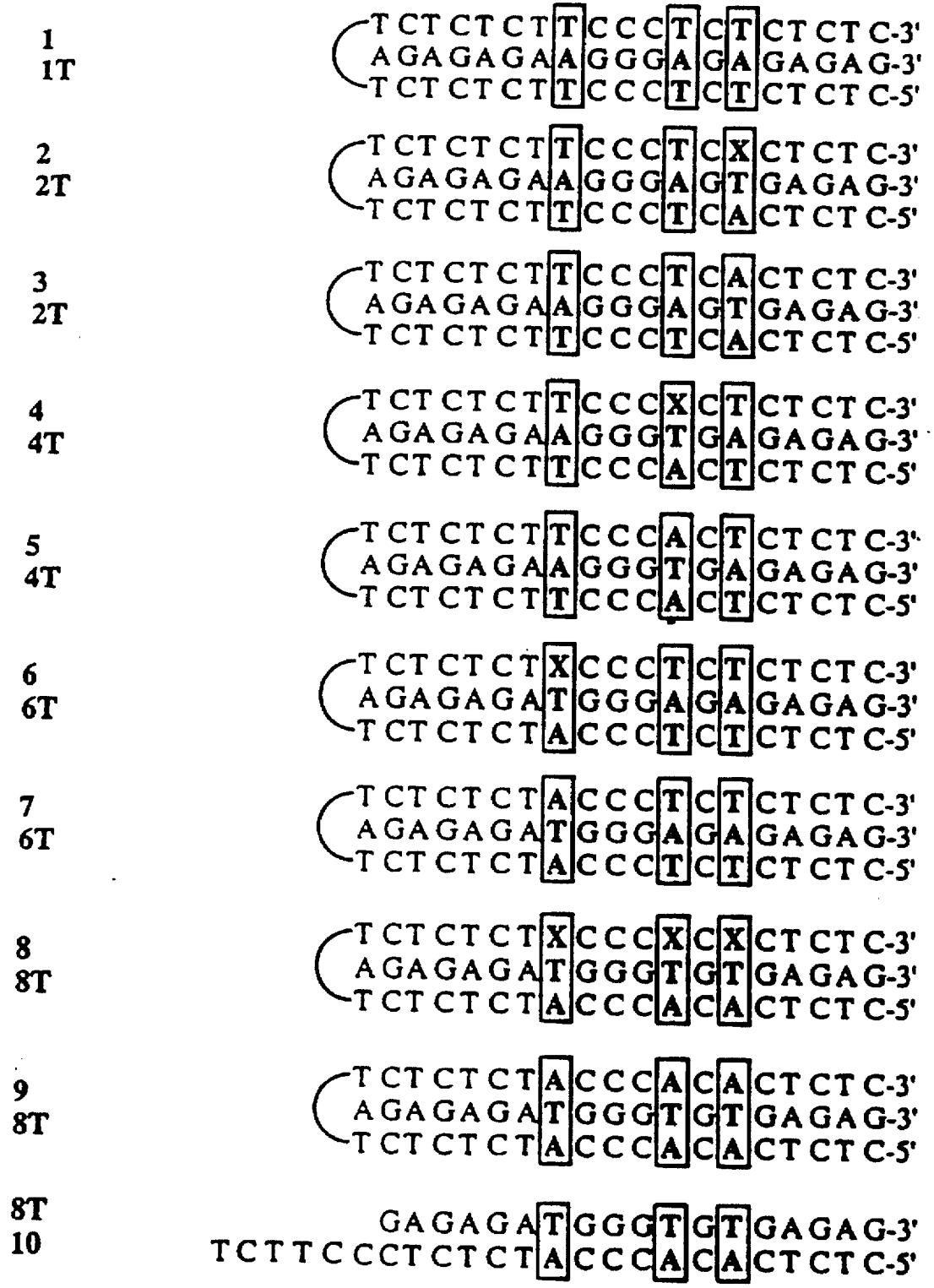
FIG. 2 displays the sequences of FTFOs and their corresponding targets; X represents the 2-aminobutyl-1,3-propanediol linker; the loop represents the pentanucleotide linker sequence -CTCTC-; the boxed nucleotides comprise the triplets studied.
Figure 3:
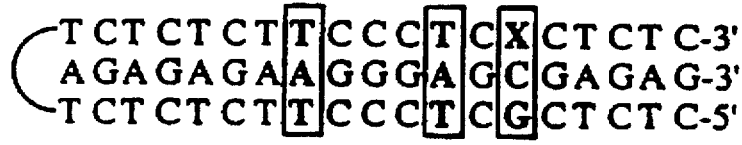
FIG. 3 displays the sequences of a second set of FTFOs and their corresponding targets; X represents the 2-aminobutyl-1,3-propanediol linker; the loop represents the pentanucleotide linker sequence -CTCTC-; the boxed nucleotides comprise the triplets studied.
Figure 3:
Figure 3:
Figure 3:
Figure 3:
Figure 3:
Figure 3:

We selected a 19 base long sequence from the initiation codon region of gag mRNA of the HIV-I genome as a target for these experiments. FIG. 1B. It is a purine-rich sequence with three pyrimidine base interruptions at base sites 8, 12 and 14 (counted from the 5'-end). FIG. 1B. A phosphorothioate oligonucleotide of 25 bases long that encompasses the current target site has antiviral activity against HIV-1 and has been the subject of human clinical trials. Agrawal & Tang, *Antisense Res. Dev.,* supra. We attempted to target the same site through "traditional" foldback triplex formation but were not successful because of the presence of the three pyrimidine bases, which, as described before, are difficult to target by triplex formation (Kandimalla and Agrawal, *Gene,* supra). To overcome the problem of pyrimidine bases in the target, we synthesized several foldback triplex-forming oligonucleotides and placed an abasic linker in the Hoogsteen domain (third strand) as a "null" or "skipping residue" against T:A or C:G base pairs. FIGS. 2 and 3. These new oligonucleotides contained one to three 2-aminobutyl-1,3-propanediol linkers (FIG. 1A) in the Hoogsteen domain opposite to pyrimidine nucleotides (T or C) in the target sequence (FIG. 1A). For comparison, we also synthesized and studied several control oligonucleotides without the linker, with perfectly matched, or with mismatched bases, as shown in FIGS. 2 and 3.

Example 2

UV Thermal Melting Studies

Figure 4:
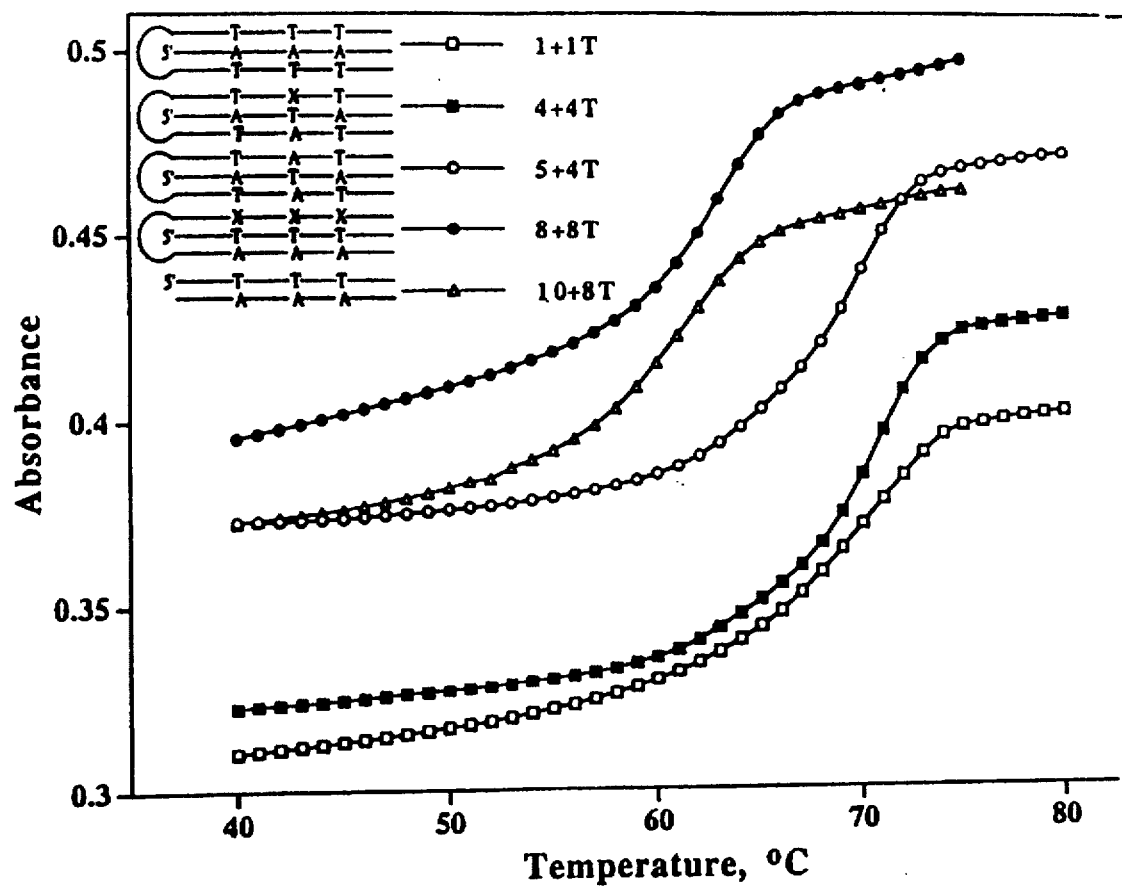
FIG. 4 displays the thermal melting curves of representative foldback triplexes and a control duplex.

We performed UV thermal melting experiments on oligonucleotide complexes with their targets in order to study the effect of abasic linkers on foldback triplex formation. UV thermal melting curves at 260 nm were determined at a heating rate of 0.5° C./min with a Perkin-Elmer (Norwalk, Conn.) Lambda 2 spectrophotometer in 100 mM sodium acetate, pH 5.0 buffer containing 10 mM magnesium chloride. The oligonucleotide concentration was 1.5 µM in each strand. The mid-point of the thermal melting curves (T$_m$) was determined from first derivative curves obtained by plotting the d(A$_{260}$)/dT versus T. The results are given in FIG. 12. Each value reported is an average of two individual experiments. The uncertainties in the T$_m$ values were estimated to be less than ±0.5° C. Oligonucleotide SEQ ID NO 1 is an ideal FTFO that contains all perfectly matched pyrimidine bases in the Hoogsteen domain. The foldback triple helix complex of oligonucleotide SEQ ID NO 1 and polypurine target stand SEQ ID NO 16 showed a T$_m$ of 70.9° C. with a sharp, cooperative, single melting transition. FIG. 4. The duplex of oligonucleotide SEQ ID NO 10 and its target strand SEQ ID NO 20, which has a similar base composition, showed a T$_m$ of 61.3° C. FIG. 4. The difference of 9.5° C. in thermal stability between the foldback triplex (SEQ ID NO 1 with SEQ ID NO 16) and the corresponding Watson-Crick double helix (SEQ ID NO 10 with SEQ ID NO 20) suggests tight binding of the Hoogsteen domain of the foldback oligonucleotide in the major groove. Kandimalla and Agrawal, *Gene,* supra. Our previous results demonstrated that an oligonucleotide containing a mismatched Hoogsteen domain will have a lower T$_m$ than the corresponding duplex because of the unbound Hoogsteen domain. Id.

In oligonucleotide SEQ ID NO 2 we substituted an aminobutyl-propanediol linker in the Hoogsteen domain that is matched with a T:A base pair corresponding to position 14 (from 5'-end) of the target sequence. The resulting foldback triplex with the target sequence showed a T$_m$ of 69.4° C. The foldback triplex of oligonucleotide SEQ ID NO 3 (with an adenine base matched with a T:A base pair) and target SEQ ID NO 17 had a $T_m$ of 68.8° C., which is 2.1° C. lower than the complex of SEQ ID NO 1 and SEQ ID NO 16. The lower stability could indicate loss of hydrogen bonding as well as stacking interactions that result from the presence of a mismatched adenine base in the Hoogsteen domain of oligonucleotide SEQ ID NO 3. When the adenine in oligonucleotide SEQ ID NO 3 was substituted with an aminobutyl-1,3-propanediol linker (oligonucleotide SEQ ID NO 2), the resulting foldback triplex had 0.6° C. higher thermal stability than the complex of SEQ ID NO 3 and SEQ ID NO 17. Although the difference in thermal stability is minimal (as demonstrated by molecular modeling results), it appears that the abasic linker destabilizes the complex to a lesser extent than a mismatched base. The higher thermal stability of the foldback triplex of oligonucleotide SEQ ID NO 2 with SEQ ID NO 17 could result from charge interactions between protonated amino group of the propanediol linker and bases in the target strand and/or phosphate back bone.

Similarly, in the purine-rich target oligonucleotide, a thymine base was substituted at positions 12 (SEQ ID NO 18) and 8 (SEQ ID NO 19) (counting from the 5'-end. The foldback triplexes of oligonucleotides SEQ ID NOs 5 and 7 (which match an adenine in the Hoogsteen domain to the thymine in their corresponding target strands (SEQ ID NO 18 and SEQ ID NO 19, respectively)) showed $T_m$s of 69.1° and 69° C., respectively. FIG. 4. That is about 1.8° C. lower stability than the perfectly matched triplex of oligonucleotides SEQ ID NO 1 with SEQ ID NO 16. The foldback triplexes of the oligonucleotides SEQ ID NOs 4 and 6 (which have a propanediol linker substituted for the adenines in the Hoogsteen domain) with target sequences SEQ ID NOs 18 and 19, respectively, both showed a $T_m$ of 70.5° C. (FIG. 4), which is very similar to the $T_m$ of the perfectly matched foldback triplex of oligonucleotides SEQ ID NO 1 with SEQ ID NO 16. These results show that the aminobutyl-propanediol linker is useful as a "null" site against a pyrimidine base in the formation of a stable foldback triplex. The slight differences in the $T_m$s of the complexes of SEQ ID NO 2 with SEQ ID NO 17, SEQ ID NO 4 with SEQ ID NO 18, and SEQ ID NO 6 with SEQ ID NO 19 may result from local sequence-dependent conformational effects near the flexible linker group.

We synthesized two oligonucleotides, one with three adenine bases (SEQ ID NO 9) and the other with three amino propanediol linkers (SEQ ID NO 8) in the Hoogsteen domain in all three positions studied, to examine how many pyrimidine sites can be tolerated in a 19 base purine-rich sequence. The foldback triplex complexes of oligonucleotides SEQ ID NOs 8 and 9 with their target sequence SEQ ID NO 20 showed $T_m$s of 63° C. and 61.5° C., respectively. FIG. 4. In earlier studies we showed that the duplex of an oligonucleotide that had a mismatched Hoogsteen domain results in lower stability than the Watson-Crick complement duplex. Id. The $T_m$ of 61.5° C. for the complex of SEQ ID NO 9 with SEQ ID NO 20 compared to the $T_m$ of 61.3° C. for the duplex of SEQ ID NO 10 with SEQ ID NO 20 and to the broad melting curve for the triplex of SEQ ID NO 9 with SEQ ID NO 20, show that the third strand (without abasic linkers) has an insignificant contribution on the stability of the complex. The amino propanediol linker-containing oligonucleotide triplex (SEQ ID NO 8 with SEQ ID NO 20), however, has a 1.5° C. higher thermal stability than the foldback triplex of SEQ ID NO 9 with SEQ ID NO 20. The gain in thermal stability of the complex of SEQ ID NO 8 with SEQ ID NO 20 over SEQ ID NO 9 with SEQ ID NO 20 likely results from the absence of destabilizing interactions (steric) or the occurrence of charge interactions between the protonated amino group of the linker and the phosphate back-bone in the former complex. The $T_m$ of the complex of SEQ ID NO 8 and SEQ ID NO 20 is 7.9° C. lower than the complex of SEQ ID NO 1 with SEQ ID NO 16 (FIG. 4), suggesting a loss of base pair hydrogen bonding and stacking interactions (Horne and Dervan, *Nucleic Acids Res.*, supra. These results indicate that multiple pyrimidine sites might not be the best choice for targeting through triplex or foldback triplex formation with abasic linker substitution. One or two pyrimidine sites in a purine-rich environment can be targeted using the abasic linker approach without losing significant binding affinity in the Py.Pu:Py motif, although up to about 5 sites can be successfully targeted even though some loss in binding affinity will be observed.

Figure 5:
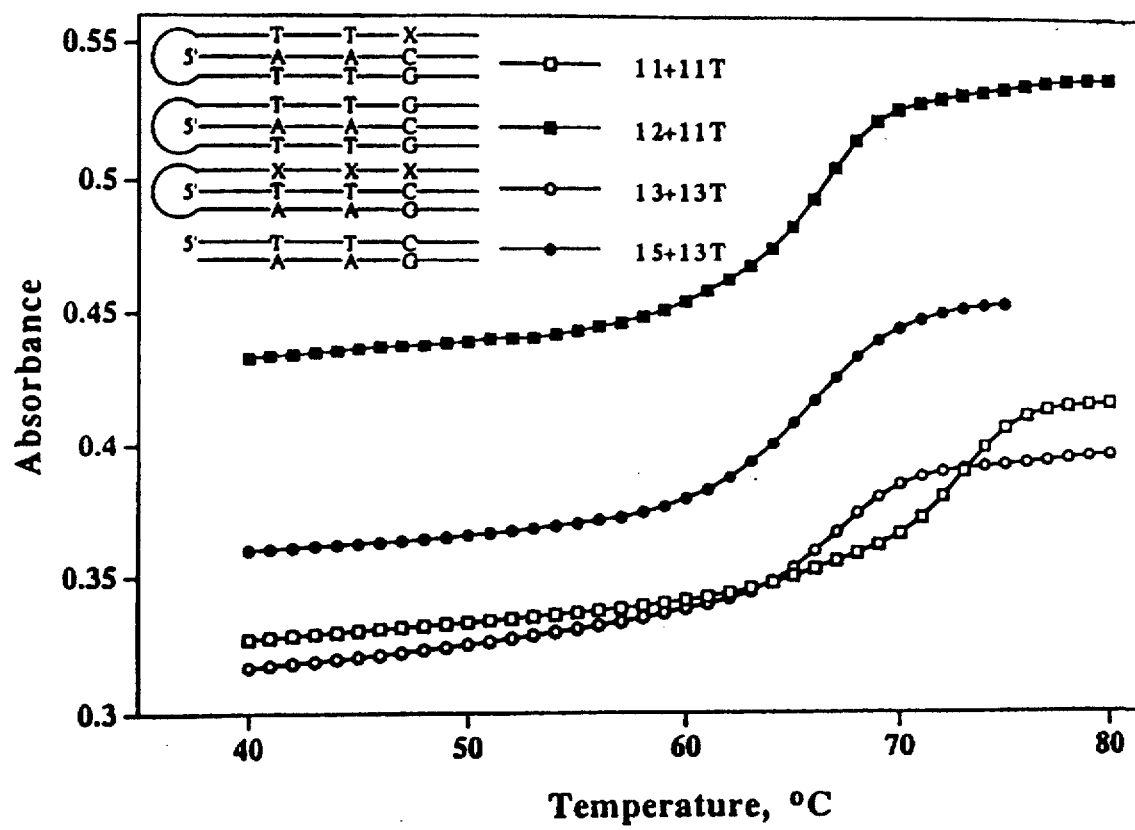
FIG. 5 displays the thermal melting curves for a second set of representative foldback triplexes and a control duplex.

The foldback triplex of oligonucleotides SEQ ID NO 12 and SEQ ID NO 21 showed a $T_m$ of 66.4° C. (FIG. 5), indicating that the presence of a G in the third strand against a C in the target strand destabilizes the complex considerably. Griffin & Dervan, *Science* 245, 967 (1989). When G in the Hoogsteen domain is substituted with the amino propanediol linker, the resulting foldback triplex of oligonucleotides SEQ ID NO 11 with SEQ ID NO 21 showed a $T_m$ of 71.8° C. FIG. 5. Thus, this $T_m$ for the complex of SEQ ID NO 11 with SEQ ID NO 21 is 5.4° C. higher than that for SEQ ID NO 12 with SEQ ID NO 21, suggesting that the propanediol linker against the C:G base pair stabilizes the triplex. The foldback triplex of oligonucleotides SEQ ID NOs 13 and SEQ ID NOs 22 has a $T_m$ of 67° C. (FIG. 5). Oligonucleotide SEQ ID NO 13 has 3 abasic linkers, one against a C:G base pair and two against two T:A base pairs. The foldback triplex of oligonucleotides SEQ ID NO 14 and SEQ ID NO 22, which has mismatched purine bases against the free pyrimidine interruptions in the target, showed a $T_m$ of 65.4° C. These results further confirm that use of an abasic linker such as propanediol over pyrimidine interruptions in the target stabilizes the triplex complex considerably compared to a mismatched base. It is clear that a mismatched purine base in the third strand destabilizes the triplex considerably. Comparison of $T_m$ s and hyperchromicity values of foldback triplexes of oligonucleotides SEQ ID NO 13 with SEQ ID NO 22 and SEQ ID NO 14 with SEQ ID NO 22 to that of the duplex of SEQ ID NO 15 with SEQ ID NO 22 (65.7° C.) (FIG. suggests that the contribution of the third strand to the stabilization of the complex is negligible in the case of the triplex of oligonucleotides SEQ ID NO 14 with SEQ ID NO 22.

Comparison of the $T_m$ of the foldback triplex of oligonucleotides SEQ ID NO 13 with SEQ ID NO 22 to that of oligonucleotides SEQ ID NO 8 with SEQ ID NO 20 ($T_m$=63° C.) further suggests that an abasic linker is more tolerated against a C:G base pair than a T:A base pair. Similarly, the foldback triplex of oligonucleotides SEQ ID NO 11 with SEQ ID NO 21 has 2.4° C. higher $T_m$ than the complex of oligonucleotides SEQ ID NO 2 with SEQ ID NO 17. These experiments suggest that i) a guanine in the third strand is sterically incompatible with a C:G base pair, as is the case of an adenine in the third strand against a T:A base pair (Mergny et al., *Biochemistry* 30, 9791 (1991)); ii) an adenine in third strand against a T:A base pair is better tolerated than a G against a C:G base pair (compare $T_m$s of the triplexes of SEQ ID NO 3 with SEQ ID NO 17 and SEQ ID NO 12 with SEQ ID NO 21); and iii) the amino propanediol linker in the third strand against a C:G base pair has a greater stabilizing effect on the triplex than against a T:A base pair (compare $T_m$s of foldback triplexes of oligonucleotides SEQ ID NO 2 with SEQ ID NO 17 verses SEQ ID NO 11 with SEQ ID NO 21) (see molecular modeling results, intra).

Figure 6:
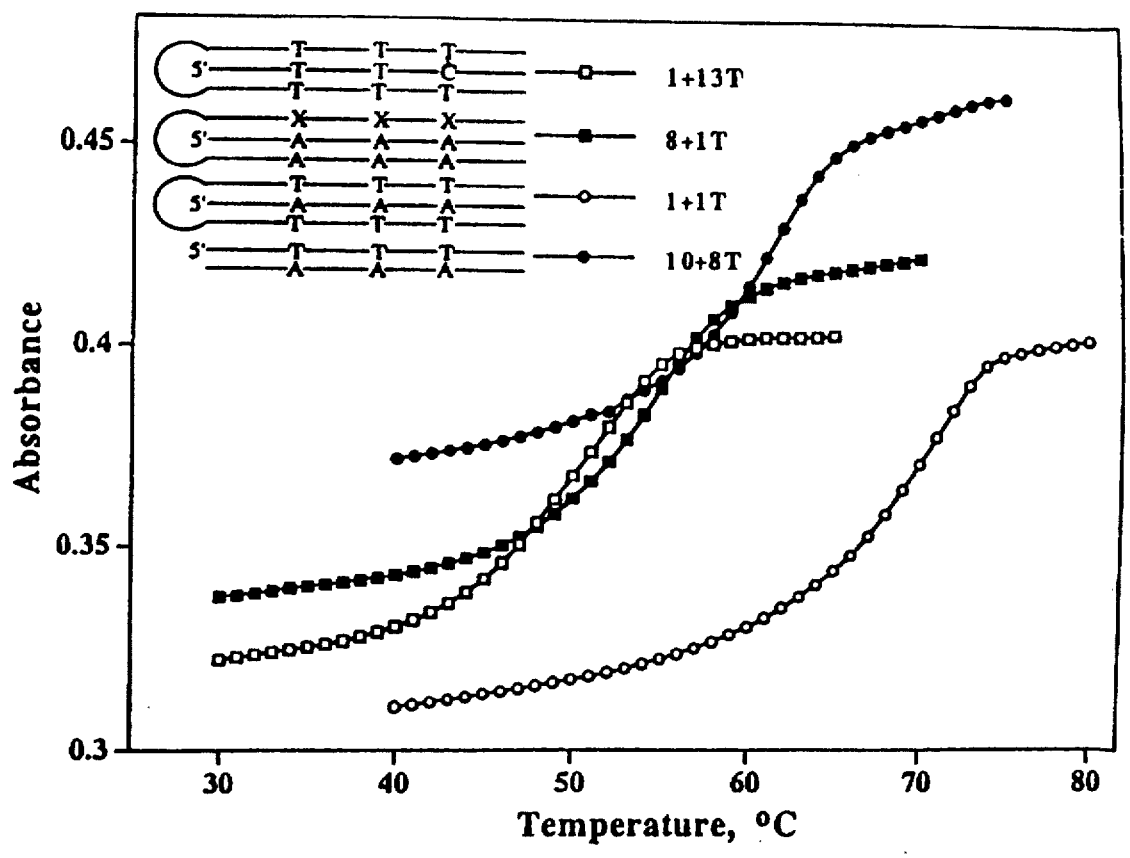
FIG. 6 displays the thermal melting curves for a third set of representative foldback triplexes and a control duplex.

To examine the sequence-specificity of FTFOs according to the invention, we measured the $T_m$s of two mismatched complexes. The complex of oligonucleotides SEQ ID NO 1 with SEQ ID NO 22 contained three mismatches each in the Watson-Crick and the Hoogsteen domains. The $T_m$ measured for this complex was 51.2° C. (FIG. 6), which is about 20° C. lower than the corresponding foldback triplex of oligonucleotides SEQ ID NO 1 with SEQ ID NO 16 (no mismatches), and 10° C. lower than the duplex of SEQ ID NO 10 with SEQ ID NO 20 (FIG. 6). The complex of oligonucleotides SEQ ID NO 8 with SEQ ID NO 16 contained three mismatches in the Watson-Crick domain and three aminobutyl-propanediol linkers in the Hoogsteen domain, which could be considered as mismatches. This complex showed a $T_m$ of 54.9° C. (FIG. 6), which is about 8.1° C. lower than the corresponding triplex (SEQ ID NO 8 with SEQ ID NO 20) with no mismatches in the Watson-Crick domain and three linkers in the Hoogsteen domain. Similarly, the triplex of SEQ ID NO 8 with SEQ ID NO 16 had a $T_m$ 6.4° C. lower than the corresponding duplex of SEQ ID NO 10 with SEQ ID NO 20 without mismatches. The higher $T_m$ for the complex of oligonucleotides SEQ ID NO 8 with SEQ ID NO 16 compared to that of the complex of oligonucleotides SEQ ID NO 1 with SEQ ID NO 22 could result from the presence of three positively charged amino groups in the former complex. This result demonstrates that the sequence-specificity of FTFOs is mainly determined by the Watson-Crick domain. The stability of triplexes depends on the base composition and experimental conditions as well as flanking sequences, however, and therefore may be different for each individual sequence.

Example 3

Molecular Modeling

Molecular modeling was performed on a Silicon Graphics Iris Indigo workstation using "INSIGHT II" program (version 2.3.1 Biosym Technologies, San Diego, Calif.). The coordinates of the target purine-rich strand were generated using the LALS program with the starting conformation as published (Raghunathan et al., *Biochemistry* 32,455 (1993)), using the linked atom least squares program (Smith & Arnott, *Acta Cryst.* a34, 3 (1978)) with helical parameters n=12 and h=3.26. The Hoogsteen strand was generated from the purine strand coordinates by a rotation of 69.5° about the helix axis. The coordinates of the Watson-Crick base paired pyrimidine chain for the triple helix was generated from the coordinates of the purine strand by applying a 2-fold symmetry operation. The Watson-Crick strand was extended at the 3'-end by five bases (CTCTC) in order to create a loop joining to the Hoogsteen strand. The backbone torsions of the loop were then adjusted to form a phosphodiester linkage with the Hoogsteen pyrimidine strand. The loop structure was minimized keeping the Watson-Crick and Hoogsteen pyrimidine strands fixed. Energy minimizations were performed using the Discover force field with 100 steps of steepest descents followed by 500 steps of conjugate gradient method in vacuum (dielectric of 1.0).

The bases in positions 8, 12, and 14 (opposite pyrimidine interruptions in the target strand) of the Hoogsteen strand were modified to have a sugar phosphate group alone (no base) or to have the abasic linker 2-aminobutyl-1,3-propanediol. The conformation of the abasic linker was determined by minimizing the triple helix structure keeping all the other residues fixed and allowing only the conformation of the abasic linker to change.

Hydrogen bonding between the amine of the linker and the bases were computed for the minimized structure. Energy minimization was performed in a vacuum (dielectric of 1.0), primarily to relieve stereochemically bad contacts. Solvent accessibility calculations were performed using a probe radius of 1.4 Å using the algorithm of Kyte and Doolittle (Kyte & Doolittle, *J. Mol. Biol.* 157, 105 (1982)). The accessibility of phosphorous atoms was not included in the calculations.

Figure 7A:
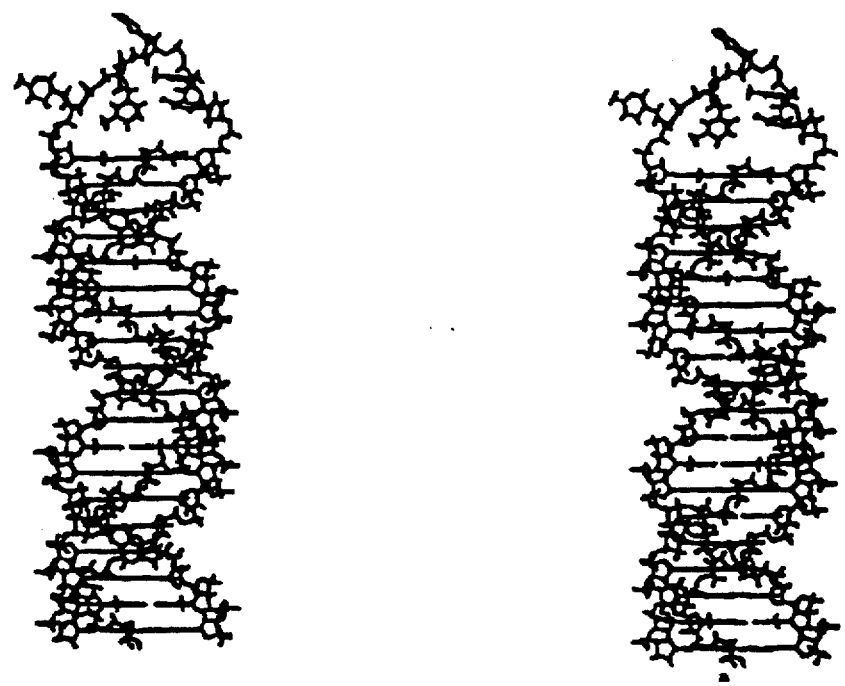
FIG. 7A displays a stereo drawing of the energy minimized foldback triplex structures of oligonucleotides SEQ ID NO 1 with SEQ ID NO 16 with matched bases in the Hoogsteen strand.

We performed the molecular modeling study to examine the loss in interaction energy that results from mismatches at the three sites studied (positions 8, 12, and 14 from the 5'-end of the target purine-rich strand). FIG. 1B. If these sites have perfectly matched base triplets, as in the complex of oligonucleotides SEQ ID NO 1 with SEQ ID NO 16, the number of hydrogen bonds would be 86 (4 for each T.A:T and 5 for each $C^+$.G:C triplet) (FIG. 7A). In addition to these interstrand hydrogen bonding interactions, intrastrand stacking interactions and sugar-base and phosphate-base interactions contribute to the stability of the complex. Whenever the purine stretch in the target sequence is interrupted by one or more pyrimidines, as in target sequences SEQ ID NO 17 with SEQ ID NO 22, the Hoogsteen strand at these sites may contain a (deoxy)ribose sugar without a base (abasic), a mismatched base that cannot form hydrogen bonds with the pyrimidine base in the target sequence, or an abasic linker such as the one shown in FIG. 1A.

Experimental and theoretical studies reported in the literature suggest that the extent of triple helix destabilization depends on the nature of the base present at the mismatched site (Griffin & Dervan, *Science* 245, 967 (1989); Horne & Dervan, *Nucleic Acids Res.*, supra; Mergny et al., *Biochemistry*, supra. The presence of a single mismatched base in the third strand results in the loss of hydrogen bonding interactions and affects the interactions of Watson-Crick base pairs already involved in the triplex. Id. Introduction of an abasic site results in the loss of hydrogen bonding interaction energy and also a significant loss in stacking energy, as the base triplets above and below the abasic site are completely exposed to solvent. Our calculations indicate that for each mismatched base pair there is an increase in the solvent-accessible area of the bases above and below the mismatched site of about 71 Å$^2$, corresponding to a loss in stabilization energy of 1.4 kcal/mole (using a conversion of 20 cal/mol/Å$^2$) (Chothia, *Nature* (London) 248, 338 (1974); Matsumara et al., *Nature* 334, 406 (1988)).

Figure 7B:
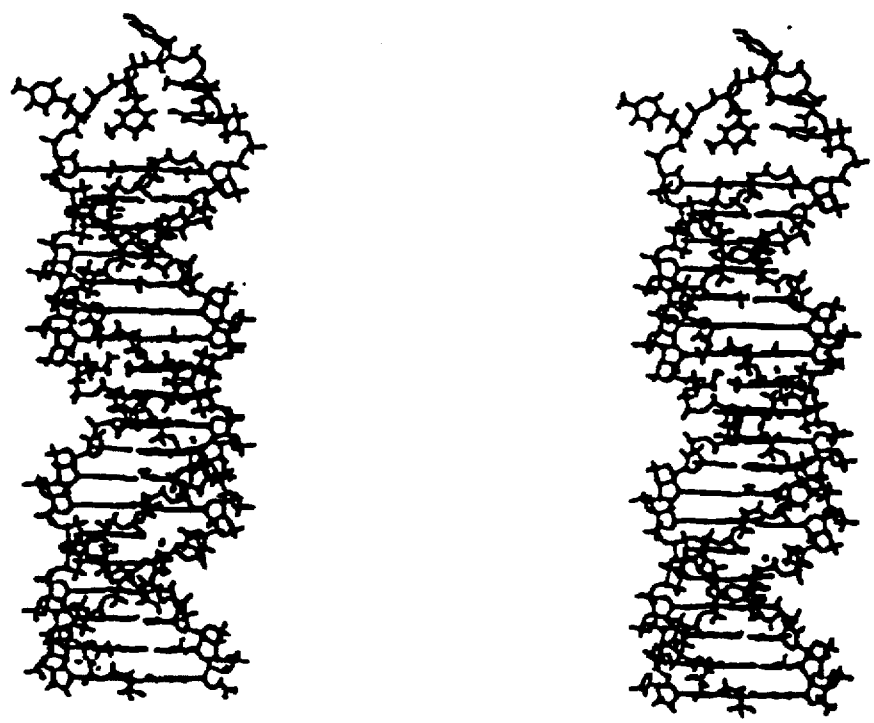
FIG. 7B displays a stereo drawing of the energy minimized foldback triplex structures of oligonucleotides SEQ ID NO 13 with SEQ ID NO 22, SEQ ID NO 13 containing three aminobutylpropanediol linkers in the Hoogsteen domain against T:A and C:G base pairs.
Figure 8B:
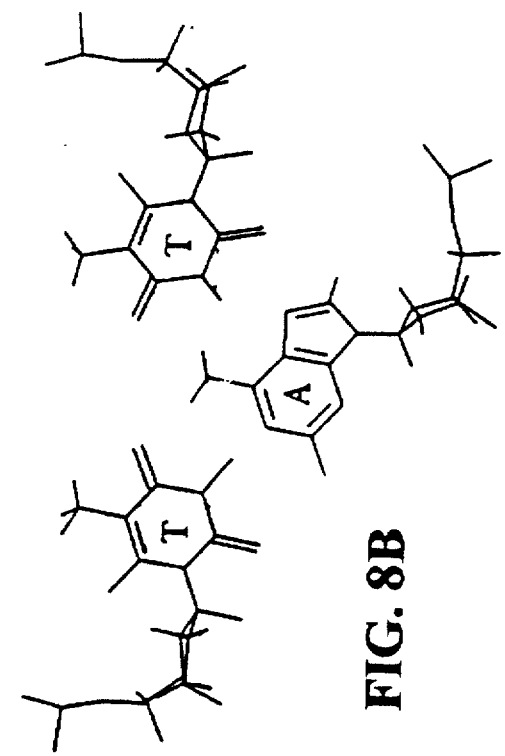
FIG. 8B displays a normal T:A.T triplet.
Figure 8D:
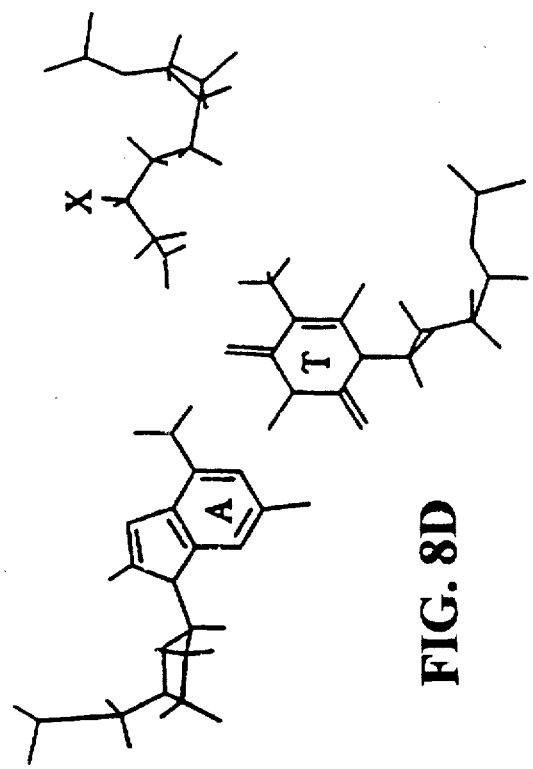
FIG. 8D displays a A:T.X triplet. All structures are energy minimized. The polarity of the sequences is indicated by the arrows in panel A.
Figure 8A:
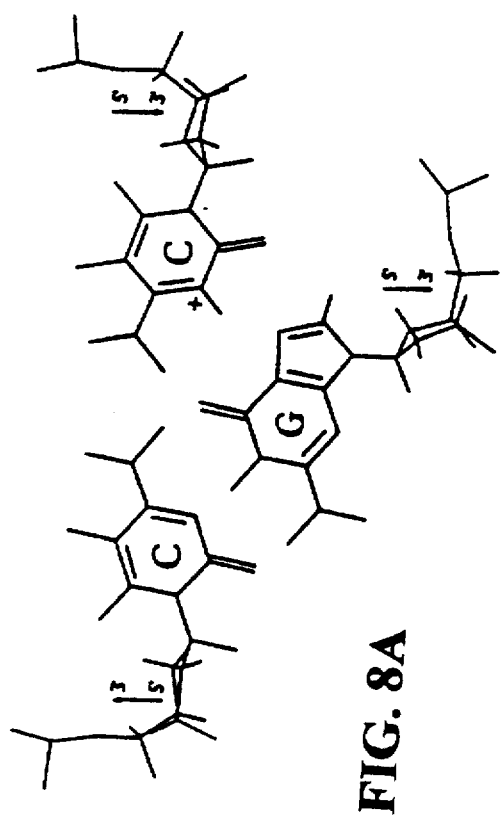
FIG. 8A displays a normal C:G.C$^+$ triplet.
Figure 8C:
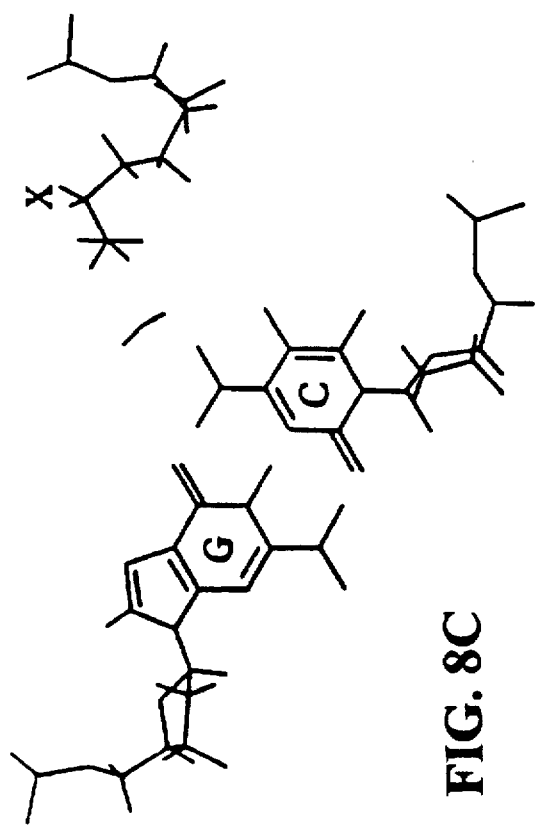
FIG. 8C displays a G:C.X triplet, wherein X is the 2-aminobutyl-1,3-propanediol linker.
Figure 9B:
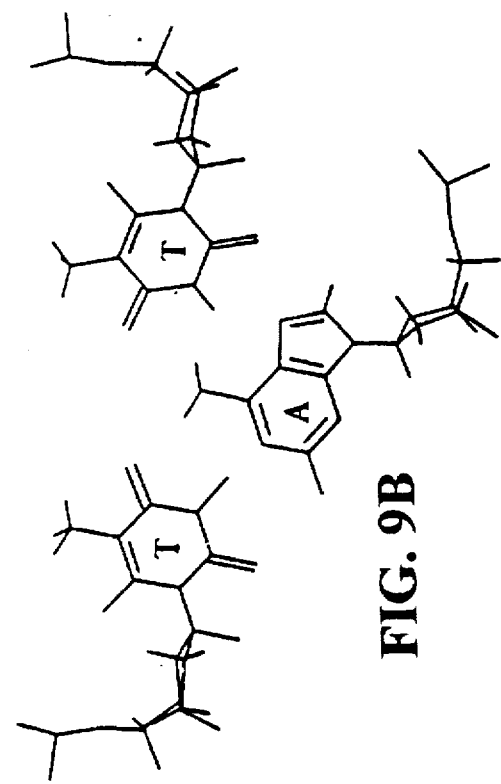
FIGS. 9A–D are the same as FIGS. 8A–D, respectively, except that X is 2-aminopropyl-1,3-propanediol linker.
Figure 9D:
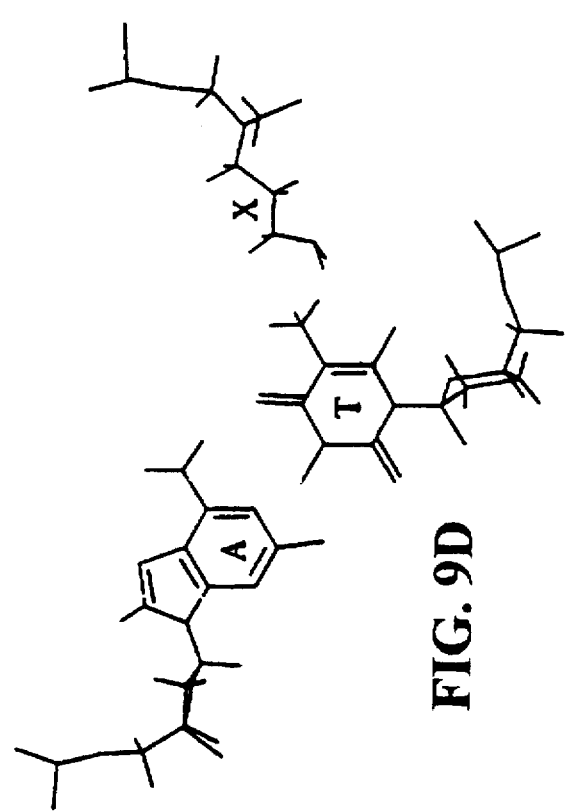
Figure 9A:
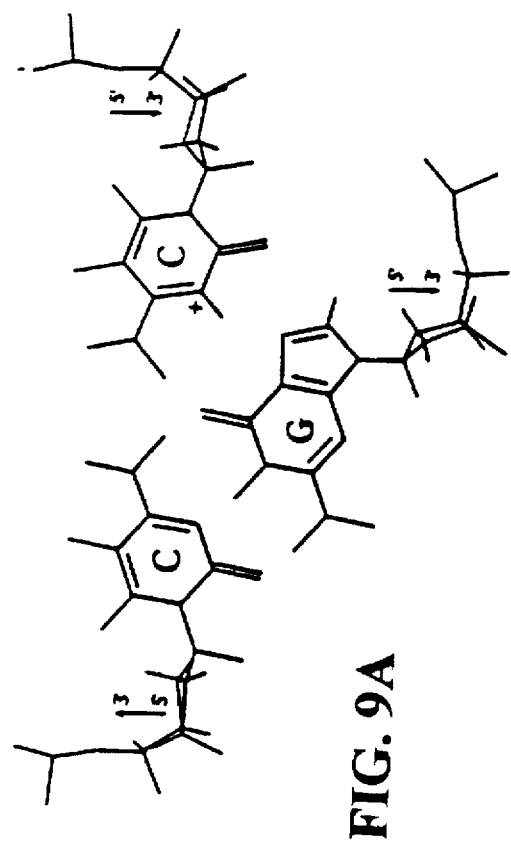
Figure 9C:
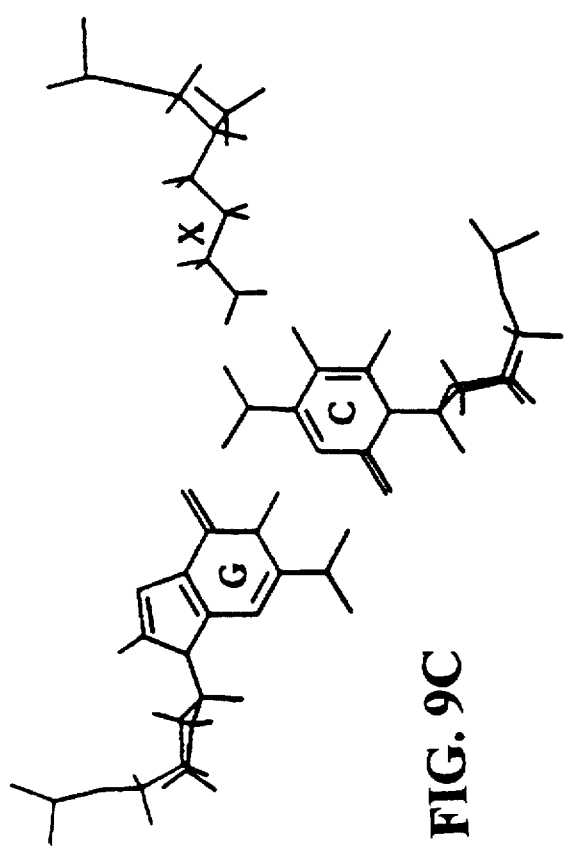

The triplex structure (SEQ ID NO 13 with SEQ ID NO 22) in which the Hoogsteen strand contains aminopropanediol abasic linkers opposite the pyrimidine interruptions in the purine-rich target strand is shown in FIG. 7B. The backbone 1,3-propanediol structure adopts a conformation very similar to the natural sugar phosphate backbone, conserving the overall geometry of the triple helical structure. The two methylene bridges joining C1' of the butyl chain with the C2 of propanediol and C1'-C2' of the butyl chain adopt an extended trans conformation while the other two linkages joining C2'-C3' and C3'-C4' of butyl chain adopt a gauche conformation (see FIG. 1A for numbering). The linker groups do not interfere with Watson-Crick hydrogen bonding at this site or the base pairing at the neighboring sites. When the linker is placed against a T:A base pair the C5-methyl group of thymine prevents hydrogen bond formation between the amino group of the linker and the O4 of thymine. The linker adopts a conformation such that no direct hydrogen bond formation between the amino group of the linker and the O4 of thymine is possible as a result of steric hindrance from the C5-methyl group of thymine. In addition, the C6-amino group of adenine restricts the available space for a solvent molecule. Any solvent molecule within this restricted space is not capable of bridging a hydrogen bond between the amine of the linker and the O4 of thymine. When the linker is placed against a C:G base pair, however, the orientation of the amine group on the abasic linker is such that a solvent molecule is capable of bridging a hydrogen bond between the amine of the linker and the N4 of cytosine. FIG. 8C. This additional hydrogen bond between the linker amino group and cytosine base explains the stabilizing effect observed in thermal melting studies when the linker is placed opposite a C:G base pair rather than a T:A base pair.

Figure 10B:
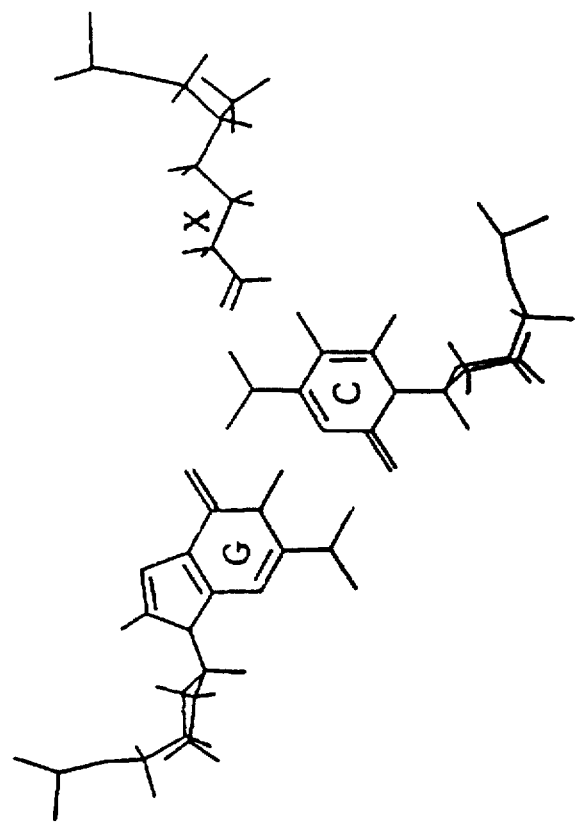
FIG. 10B displays triplex formation of the modified linker 2-butyryl-1,3-propanediol with a C:G base pair.
Figure 10A:
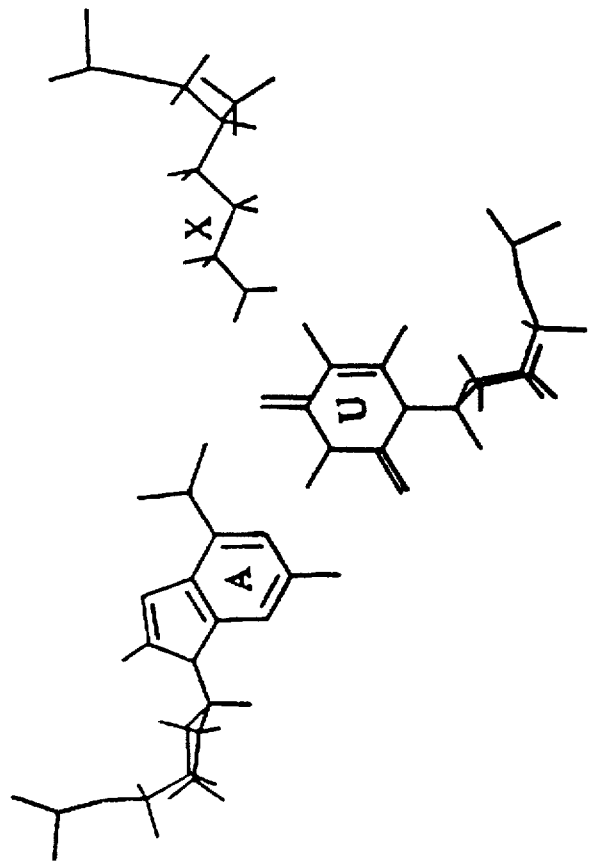
FIG. 10A displays triplex formation of the modified linker 2-aminopropyl-1,3-propanediol with a U:A base pair.

Molecular modeling studies revealed that a butyl linker, which is somewhat longer, does not fit in the major groove and hydrogen bond with the functional groups of the target pyrimidine bases as well. As a result, the linker is not able to take an extended conformation and bend to accommodate itself in the groove (see FIG. 8). Our results suggest that if we reduce the length of the side chain butyl arm by one methylene group and make a propyl-propanediol linker that can take an extended conformation, which would be the choice of linker for triplex formation rather than butyl-propanediol linker (FIGS. 9A–D). Furthermore, the molecular modeling studies suggest that if a linker is placed against a U:A base pair, the amino group of the linker can hydrogen bond with O4 of uracil without any steric hindrance, as there is no bulky methyl group present at the C5 position of uracil. FIG. 10A. Similarly, if the amino group of the linker is replaced with a carbonyl group, the oxygen of the carbonyl can directly hydrogen bond with the N4 of cytosine without any solvent mediation. FIG. 10B.

Compared to a fully matched triplex (SEQ ID NO 1 with SEQ ID NO 16), there is a loss of one hydrogen bond for every aminopropanediol linker introduced against a C:G base pair, and a loss of two hydrogen bonds for every linker introduced against a T:A base pair. In addition, the solvent-accessible area of the flanking bases of the mismatched sites increases by 60 to 80 Å$^2$, corresponding to a loss in stabilization energy of 1.2 to 1.6 kcal/mole (Chothia, supra; and Matsumara et al., supra) for each linker substitution, as compared to the perfectly matched sequence. The positive charge of the abasic linker provides additional stabilization energy. The magnitude of charge stabilization depends partially on the counter-ions. Modeling electrostatic interactions in the presence of the counter-ions of the charged groups is rather complex.

Lack of specific bases that recognize C:G and T:A base pairs in either the Hoogsteen or reverse Hoogsteen motif for stable triplex formation has limited the progress of in vivo studies on the triplex approach. Horne and Dervan reported use of 1,2-dideoxy-D-ribose that has stereochemistry similar to that of the natural nucleosides in the third strand, allowing it to "skip over" a pyrimidine base in the target sequence (Horne & Dervan, supra). They reported that the abasic site is significantly better over C:G and T:A than G:C and A:T base pairs. In a similar approach, but in Pu.Pu:Py motif, Mayfield and Miller used a propanediol linker over C:G interruptions in an otherwise G:C rich target sequence. Mayfield & Miller, *Nucleic Acids Res.*, supra. Gel mobility and DNase I experiments provided evidence for better triplex formation with oligonucleotides containing a linker than those that contained a mismatched base in the same position. Protein binding studies showed, however, that the oligonucleotide with three linkers was less effective than the control oligonucleotide. These authors offered no explanation for the loss in the efficiency of inhibition of protein binding. The results described here, however, demonstrate that the triplex with an increased number of linker moieties (>2) has lower stability, despite the fact that the positively charged amino function of the linker contributes to binding affinity. Although stability is decreased, FTFOs according to the invention having up to about 5 abasic linkers can be successfully empolyed. The introduction of an abasic site into TFOS, as above, would definitely result in significant loss of sequence-specificity. The new abasic linker described here and by Mayfield and Miller, supra, used to "skip over" a pyrimidine base in a purine-rich site may increase number of potential target sites available for foldback triplex formation.

Example 4

Cellular Uptake

Cell culture

Human T cell and leukemia cell line H9 are used in this study. They are cultured in RPMI media supplemented with 10% fetal bovine serum (heat inactivated to 56° C. for 30 minutes to inactivate the nucleases), 2 mM glutamine, 100 ml streptomycin, 100 U/ml penicillin and 6×10$^{-5}$M of 2-mercaptoethanol in an air incubator (37° C., humidified by 5% $CO_2$–95% $O_2$).

Fluorescein labeling of oligonucleotides

Fluorescein is conjugated to the 5' end of the oligonucleotides by either an automated DNA synthesizer or by a manual procedure using a "FLUORESCEIN-ON" phosphoramidite. The efficiency of fluorescein labeling is determined by using a spectrofluorometer (excitation 488 nm, emission 520 nm).

Cell uptake

The concentrations of the fluorescein labeled and unlabelled oligonucleotides in the samples are measured by a spectrofluorometer and UV spectroscopy and adjusted to be the same by adding the corresponding unlabelled oligonucleotides. Labelled oligonucleotides (0.2 OD/100 ml) are added to the cells (5×10$^6$ cells/ml, 0.5 ml) and set to culture. After 4 hours of culture, aliquots of cell culture mixtures are removed, washed, and resuspended in Hank's balanced salt solution (HBSS) supplemented with 0.1% BSA and 0.1% sodiun azide. Propidium iodide (final concentration 10 µl/ml) is used to distinguish viable cells from dead cells. Flow cytometric data on 5,000 viable cell is acquired in list mode on Epics XL (Coulter, Hialeah, Fla.), and data are analyzed by Epics XL (version 1.5 software) after gating on living cells by forward scatter versus side scatter and propidium iodide staining.

The results demonstrate that oligonucleotides according to the invention are taken up by cells.

Example 5

DNase I Hydrolysis Assay

Spectrophotometric method

DNase I is an endonuclease that hydrolyzes deoxyribonucleic acids in the presence of magnesium ions to the mononucleotide level without much sequence selectivity. Double stranded DNA is a perfect substrate and to some extent single stranded DNA is also hydrolyzed. When DNA is hydrolyzed to short pieces and monomers, absorbance of DNA at 260 nm will increase. In this experiment the extent of absorbance increase with time due to hydrolysis of double and single stranded oligonucleotides by DNase I is measured. DNase I does not hydrolyze triple stranded DNA structures.

Samples are prepared in buffers of 100 mM sodium acetate, pH 5.0 and 7.4; 100 mM sodium acetate and 10 mM magnesium chloride, pH 5.0 and 6.5. 0.2 $A_{260}$ units of each antisense oligonucleotide are mixed with equal amounts of target nucleic acid and dried in speed vac. The dried oligonucleotides are dissolved in appropriate buffer, heated to 95° C. for 10 min, allowed to come to room temperature slowly and then left at 4° C. overnight. Each sample is equilibrated at 20° C. for 10 minutes, 4 units of DNase I is added and mixed, and absorbance at 260 nm as a function of time recorded on a Perkin-Elmer Lambda 2 Spectrophotometer.

Hydrolysis patterns of single, double, and triple stranded structures with time demonstrate that oligonucleotides of the invention are highly resistant to DNase I action, indicating a structure that is different than single and double strands. Oligonucleotides that form only duplexes are hydrolysed quickly, however. Also the target oligonucleotide, which is a single strand, is digested, but at slower rate than the double strands.

Gel electrophoresis method

An oligonucleotide according to the invetion is 5'-end labeled with $^{32}P$. A target sequence is also 5'-end labeled with $^{32}P$ using T4 polynucleotide kinase. End labeled oligonucleotides equivalent to 3000–5000 cpm are added to the appropriate amount of the same cold oligonucleotide to bring the concentration to 0.2 $A_{260}$ units, mixed with equal amounts of antisense oligonucleotides according to the invention in 100 mM sodium acetate, pH 5.0, 10 mM magnesium chloride buffer, heated to 95° C., cooled, and left overnight at 4° C. as described. Each sample is then treated with 2 units of DNase I for 10 min at 20° C. and the hydrolysis products are analyzed on a 20% denaturing polyacrylamide gel containing 7M urea.

Autoradiography will demonstrate the hydrolytic pattern of different complexes in the presence of DNase I and show that single and double strand structures of oligonucleotides are digested completely. By contrast, the foldback triplex structures formed with oligonucleotides according to the invention will be seen to be highly resistant to nuclease attack.

Example 6

The following assays are used to measure the ability of the oligonucleotide of the invention to inhibit HIV-1 replication.

Syncytia Assay

The ability of the oligonucleotides of the invention to inhibit HIV-1 replication, and thus syncytia formation, in tissue culture is tested in T cell cultures according to the method of Agrawal and Sarin, Advanced Drug Delivery Rev. 6, 251 ( 1991 ). Briefly, CEM cells are infected with HIV-1 virions (0.01–0.1 $TCID_{50}$/cell) for one hour at 37° C. After one hour unadsorbed virions are washed and the infected cells are divided among walls of 24 well plates. To the infected cells, an appropriate concentration (from stock solution) of oligonucleotide is added to obtain the required concentration in 2 ml medium. The cells are then cultured for three days. At the end of three days, infected cells are examined visually for syncytium formation or stained with trypan blue or CTT for cytopathic effect determination.

The results demonstrate that oligonucleotides according to the invention inhibit syncitia formation.

p24 Expression Assay

HIV expression can be determined by measuring the level of viral protein p24 expression in CEM cells essentially as described by Agrawal and Sarin, supra. Briefly, cells are pelleted and then resuspended in phosphate saline at a concentration of about $10^6$/ml. The cells are spotted on toxoplasmosis slides, air dried, and fixed in methanol/ acetone (1:1) for 15 min at room temperature (RT). The slides are next incubated with 10% normal goat serum at RT for 30 min and washed with phosphate buffered saline (PBS). Anti-p24 monoclonal antibody is added to each well, and the slides are incubated in a humid chamber at 37° C. The slides are labelled with goat anti-mouse IgG for 30 min and then washed in PBS overnight. The percentage of cells fluorescing in oligonucleotide-treated and untreated cells is compared.

The results demonstrate that oligonucleotides according to the invention substantially and significantly reduce p24 expression.

Cytopathic Effect (CPE)

HIV-induced cytopathic effect is determined by measuring the decrease in the number of viable cells after infection. The cells are counted by adding MTT or trypan blue dye to the cells and determining how many cells (dead) take up the dye. The assay is done in triplicate.

The results demonstrate that oligonucleotides according to the invention will reduce the viral cytopathic effect.

Reverse Transcriptase Assay

This assay is performed essentially as described in Agrawal and Sarin, supra. Supernatants from virus-infected cultures in the presence and absence of oligonucleotide are collected and virus particles precipitated with poly (ethyleneglycol). The virus pellet is suspended in 300 µl of buffer containing 50 mM Tris-HCl (pH 6.8), 5 mM dithiothreitol (DTT), 250 mM KCl, and 25% Triton X-100. Reverse transcriptase activity in the solubilized pellet is assayed in a 50 µl reaction mixture containing 50 mM Tris-HCl (pH 7.8), 5 mM DTT, 100 mM KCl, 0.01% Triton X-100, 5 µg dt15.rAn as template primer, 10 mM MgCl2, 15 µM [$^3$H]dTTP (15 Ci/mmol), and 10 µl of the disrupted virus suspension. After incubation for 1 hr at 37° C. and subsequent addition of 50 µg yeast tRNA, the incorporation into the cold trichloroacetic acid-insoluble DNA fraction is assayed by counting in a β scintillation counter.

The results demonstrate that oligonucleotides according to the invention inhibit reverse transcriptase.

We claim:

1. A foldback triplex-forming oligonucleotide comprising a duplex forming region, a triplex forming region, and a linker region, wherein the duplex forming region is complementary to a region of a target nucleic acid and hybridizes to that region, thereby forming a duplex, and wherein the triplex forming region is complementary to the duplex forming region and hybridizes with the duplex formed between the duplex forming region and the target nucleic acid and thereby forms a triplex, and wherein the triplex forming region also comprises one or two abasic linkers that match up against a pyrimidine nucleotide of the target sequence, and wherein the linker region comprises a single covalent linkage or a flexible chemical moiety that connects the duplex forming region and the triplex forming region.

2. The foldback triplex-forming oligonucleotide according to claim 1, wherein the abasic linker has the structure:

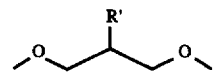

where R' is $NH_2(CH_2)_4-$, $NH_2(CH_2)_3-$, $NH_2CH_2CH=CH-$, $NH_2CH=CH-$, $RCO(CH_2)_3-$, $RCOCH_2CH=CH-$, $RCOCH=CH-$, wherein R is $-H$, $-OH$, $-NH_2$, $-CH_3$, or $-C_2H_3$.

3. The foldback triplex-forming oligonucleotide according to claim 2, wherein R' is 4-aminobutyl or 4-aminopropyl.

4. The foldback triplex-forming oligonucleotide according to claim 1, wherein the duplex forming region comprises from about 8 to about 50 nucleotides.

5. The foldback triplex-forming oligonucleotide according to claim 1, wherein the duplex forming region comprises from about 12 to about 35 nucleotides.

6. The foldback triplex-forming oligonucleotide according to claim 5, wherein the abasic linker has the structure:

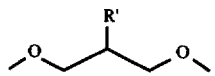

where R' is $NH_2(CH_2)_4-$, $NH_2(CH_2)_3-$, $NH_2CH_2CH=CH-$, $NH_2CH=CH-$, $RCO(CH_2)_3-$, $RCOCH_2CH=CH-$, $RCOCH=CH-$, wherein R is $-H$, $-OH$, $-NH_2$, $-CH_3$, or $-C_2H_3$.

7. The foldback triplex-forming oligonucleotide according to claim 6, wherein R' is 4-aminobutyl.

8. The foldback triplex-forming oligonucleotide according to claim 5, wherein the triplex-forming region comprises from about 8 up about 34 monomers, which monomers comprise a nucleotide or an abasic linker.

9. The foldback triplex-forming oligonucleotide according to claim 8, wherein the abasic linker has the structure:

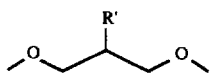

where R' is $NH_2(CH_2)_4-$, $NH_2(CH_2)_3-$, $NH_2CH_2CH=CH-$, $NH_2CH=CH-$, $RCO(CH_2)_3-$, $RCOCH_2CH=CH-$, $RCOCH=CH-$, wherein R is $-H$, $-OH$, $-NH_2$, $-CH_3$, or $-C_2H_3$.

10. The foldback triplex-forming oligonucleotide according to claim 9, wherein R' is 4-aminobutyl or 4-aminopropyl.

11. The foldback triplex-forming oligonucleotide according to claim 8, wherein the linker region comprises a oligonucleotide of from about 3 to about 10 nucleotides, a substituted or unsubstituted alkyl or aryl group having about 4 to 20 carbon atoms, or a ribose or 1',2'-dideoxyribose chain having from 1 to about 3 monomers.

12. The foldback triplex-forming oligonucleotide according to claim 11, wherein the linker region comprises a pentanucleotide or hexaethyleneglycol.

13. The foldback triplex-forming oligonucleotide according to claim 12, wherein the abasic linker has the structure:

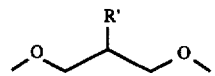

where R' is $NH_2(CH_2)_4-$, $NH_2(CH_2)_3-$, $NH_2CH_2CH=CH-$, $NH_2CH=CH-$, $RCO(CH_2)_3-$, $RCOCH_2CH=CH-$, $RCOCH=CH-$, wherein R is $-H$, $-OH$, $-NH_2$, $-CH_3$, or $-C_2H_3$.

14. The foldback triplex-forming oligonucleotide according to claim 13, wherein R' is 4-aminobutyl or 4-aminopropyl.

* * * * *